US008043622B2

(12) United States Patent
Klinman et al.

(10) Patent No.: US 8,043,622 B2
(45) Date of Patent: Oct. 25, 2011

(54) METHOD OF TREATING INFLAMMATORY LUNG DISEASE WITH SUPPRESSORS OF CPG OLIGONUCLEOTIDES

(75) Inventors: Dennis M. Klinman, Potomac, MD (US); Hiroshi Yamada, Kanagawa (JP)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 860 days.

(21) Appl. No.: 10/682,130

(22) Filed: Oct. 7, 2003

(65) Prior Publication Data
US 2004/0132682 A1 Jul. 8, 2004

Related U.S. Application Data

(60) Provisional application No. 60/417,263, filed on Oct. 8, 2002.

(51) Int. Cl.
*A61K 39/38* (2006.01)
*C07H 19/00* (2006.01)
*C07H 21/00* (2006.01)
(52) U.S. Cl. .................................. 424/184.1; 536/22.1
(58) Field of Classification Search .................... 514/44; 536/23.1
See application file for complete search history.

(56) References Cited

U.S. PATENT DOCUMENTS

| | | | |
|---|---|---|---|
| 4,469,863 | A | 9/1984 | Ts'o et al. |
| 5,023,243 | A | 6/1991 | Tullis |
| 5,663,153 | A | 9/1997 | Hutcherson et al. |
| 6,214,806 | B1 * | 4/2001 | Krieg et al. ................. 514/44 |
| 7,094,766 | B1 | 8/2006 | Gilchrest et al. |
| 2003/0087848 | A1 | 5/2003 | Bratzler et al. |
| 2004/0132682 | A1 | 7/2004 | Klinman et al. |
| 2004/0248834 | A1 | 12/2004 | Klinman et al. |
| 2006/0074039 | A1 | 4/2006 | Klinman et al. |

FOREIGN PATENT DOCUMENTS

| | | |
|---|---|---|
| EP | 0 092 574 | 4/1992 |
| WO | WO 83/01451 | 4/1983 |
| WO | WO/93/23572 | * 11/1993 |
| WO | WO 95/26204 | 9/1995 |
| WO | WO 96/02555 | 2/1996 |
| WO | WO 98/11211 | 3/1998 |
| WO | WO 98/18810 | 5/1998 |
| WO | WO 98/37919 | 9/1998 |
| WO | WO 98/40100 | 9/1998 |
| WO | WO 98/52581 | 11/1998 |
| WO | WO 99/51259 | 10/1999 |
| WO | WO 03/027313 | 4/2003 |
| WO | WO 2004/012669 | 2/2004 |

OTHER PUBLICATIONS

Broide et al 1998. Immunostimulatory DNA sequences inhibit IL-5, eosinophilic inflammation, and airway hyperresponsiveness in mice. J. Immunol. 161: 7054-7062.*
Bernard G Am J Respir Crit Care Med. Oct. 1, 2005;172(7):798-806. Epub Jul. 14, 2005.*
Van der Vliet A, Eiserich JP, Cross CE 2000. Nitric oxide: a pro-inflammatory mediator in lung disease? Respir Res 1: 67-72.*
Matthay MA, Zimmerman GA, Esmon C, et al. Future research directions in acute lung injury:summary of a National Heart, Lung, and Blood Institute working group. Am J Respir Crit Care Med 2003;167:1027-1035.*
Goldberg, B, Urnovitz, HB, Stricker, RB: Beyond danger: Unmethylated CpG dinucleotides and the immunopathogenesis of disease. Immunol Lett 2000 73:13-18.*
Heeg K, Zimmermann S. CpG DNA as a Th1 trigger [Review]. Int Arch Allergy Immunol 2000;121:87-97.*
Battegay, "Angiogenesis: mechanistic insignts, neovascular diseases, and therapeutic prospects," *J. Molec. Med.* 73(7): 333-346, 1995.
Beck et al., "Vascular development: cellular and molecular regulation," *FASEB J.* 11(5):365, 1997.
Bjersing et al., "Anti-proliferative effects of phosphodiester oligodeoxynucleotides," *Immunobiology*, 209(8):637-45, 2004.
Braun et al.,"On the Difficulties of Establishing a Consensus on the Definition of and Diagnostic Investigations for Reactive Arthritis," *J. Rheumatol.* 27:2185-2192, 2000.
Britigan et al., "Lactoferrin Binds CpG-Containing Oligonucleotides and Inhibits Their Immunostimulatory Effects on Human B Cells," *J. Immunol.* 167:2921-2928, 2001.
Chen et al., "Identification of methylated CpG motifs as inhibitors of the immune stimulatory CpG motifs," *Gene Ther.* 8(13):1024-1032, 2001.
Deng et al., "Intra-articularly localized bacterial DNA containing CpG motifs induces arthritis," *Nat. Med.* 5:702-705, 1999.
Deng et al., "Synovial cytokine mRNA expression during arthritis triggered by CpG motifs of bacterial DNA," *Arthritis Res.* 3(1):48-53, 2001.
Deng et al., "The Features of Arthritis Induced by CpG Motifs in Bacterial DNA," *Arthritis Rheum.* 43:356-364, 2000.
Gaudric et al. "Quantification of Angiogenesis due to Basic Fibroblast Growth Factor in a Modified Rabbit Corneal Model," *Ophthal. Res.* 24: 181, 1992.
Gursel et al., "Sterically Stabilized Cationic Liposomes Improve the Uptake and Immunostimulatory Activity of CpG Oligonucleotides,"*J. Immunol.* 167: 3324, 2001.
Gürsel et al., "Differential and competitive activiation of human immune cells by distinct classes of CpG oligodeoxynucleotide," *J. Leuko.Biol.* 71:813-820, 2002.
Han et al., "G-quadruplex DNA: a potential target for anti-cancer drug design," *Trends Pharmacol. Sci.* 21:136-142, 2000.
Hartmann et al., "CpG DNA: A potent signal for growth, activation, and maturation of human dendritic cells," *Proc. Natl. Acad. Sci. USA* 96:9305-9310, 1999.
Ho et al., "An Immunomodulatory GpG Oligonucleotide for the Treatment of Autoimmunity via the Innate and Adaptive Immune Systems," *J. Immunol.* 171:4920-4926, 2003.

(Continued)

*Primary Examiner* — Nita M Minnifield
*Assistant Examiner* — Nina Archie
(74) *Attorney, Agent, or Firm* — Klarquist Sparkman, LLP

(57) ABSTRACT

The present disclosure relates to oligodeoxynucleotides that suppress an immune response. Methods are disclosed for inhibiting or treating inflammatory lung disease by administering a therapeutically effective amount of a suppressive oligodeoxynucleotide.

29 Claims, 8 Drawing Sheets

OTHER PUBLICATIONS

Kenyon et al., "A Model of Angiogenesis in the Mouse Cornea," *Invest Opthalmol. Vis. Sci.* 37:1625-1632, 1996.

Klinman et al., "CpG Motifs present in bacterial DNA rapdily induce lymphocytes to secrete interleukin 6, interleukin 12, and interferon γ," *Proc. Natl. Acad. Sci.* USA 93:2879, 1996.

Klinman et al., "Contribution of CpG Motifs to the Immunogenicity of DNA Vaccines," *J.Immunol.* 158:3635-3639, 1997.

Klinman et al., "Activation of the innate immune system by CpG oligodeoxynucleotides: immunoprotective activity and safety," *Springer•Semin. Immunopathol.* 22:173-183, 2000.

Krieg et al., "CpG motifs in bacterial DNA trigger direct B-cell activation," *Nature* 374:546-549, 1995.

Krieg, "Commentary: A possible cause of joint destruction in septic arthritis," *Arthritis Research* 1(1):3-4, 1999.

Krieg, "From bugs to drugs: therapeutic immunomodulation with oligodeoxynucleotides containing CpG sequences from bacterial DNA," *Antisense Nucleic Acid Drug Dev* 11(3):181-188; 2001.

Krieg et al., "Enhancing vaccines with immune stimulatory CpG DNA," *Curr Opin Mol Ther* 3(1):15-24, 2001.

Krieg, "From A to Z on CpG," *Trends Immunol.* 23(2):64-65, 2002.

Krieg, "CpG Motifs in bacterial DNA and their immune effects," *Annu Rev Immunol* 20:709-760, 2002.

Lenert et al., "CpG stimulation of primary mouse B cells is blocked by inhibitory oligodeoxyribonuceotides at a site proximal to NF-kappaB activation." *Antisense Nucleic Acid Drug Dev* 11(4):247-256, 2001.

Liang et al., "Activation of Human B Cells by Phosphorothioate Oligodeoxynucleotides," *J. Clin. Invest.* 98:1119-1129, 1996.

Lichtenberg et al., "The Rat Subcutaneous Air Sac Model: A Quantitative Assay of Antiangiogenesis in Induced Vessels," *Pharmacol Toxicol.* 84:34-40, 1999.

Murchie et al., "Tetraplex folding of telomere sequences and the inclusion of adenine bases," *EMBO J.* 13:993-1001, 1994.

Pisetsky et al., "Immunological Properties of Bacterial DNA," *NY Acad. Sci.* 772:152-163, 1995.

Pisetsky et al., "Inhibition of Murine Macrophage IL-12 Production by Natural and Synthetic DNA," *Clin. Immunol.* 96, 198-204, 2000.

Quarcoo et al., "Inhibition of signal transducer and activator of transcription 1 attenuates allergen-induced airway inflammation and hyperreactivity," *J Allergy Clin Immunol.*, 114(2):288-95, 2004.

Roman et al., "Immunostimulatory DNA sequences function as T helper-1-promoting adjuvants," *Nature Medicine* 3(8):849-854, 1997.

Stunz et al., "Inhibitory oligonucleotides specifically block effects of stimulatory CpG oligonucleotides in B cells," *Eur J Immunol* 32(5):1212-1222; 2002.

Verthelyi et al., "Human Peripheral Blood Cells Differentially Recognize and Respond to Two Distinct CpG Motifs," *J. Immunol.* 166:2372-2377, 2001.

Vialas et al., "Oxidative Damage Generated by an Oxo-Metalloporphyrin onto the Human Telomeric Sequence," *Biochemistry* 39:9514-9522, 2000.

Wilting et al., "A modified chorioallantoic membrane (CAM) assay for qualitative and quantitative study of growth factors," *Anat. Embryol.* 183: 259-271, 1991.

Yamada et al., "Effect of Suppressive DNA on CpG-Induced Immunce Activation," *J. Immunol.* 169:5590-5594, 2002.

Yamamoto et al., "Unique Pallindromic Sequences in Synthetic Oligonucleotides are Required to Induce INF and Augment INF-Mediated Natural Killer Activity," *J. Immunol.* 148:4072-4076, 1992.

Yi et al., "Rapid Immune Activation by CpG Motifs in Bacterial DNA," *J. Immun.* 157:5394-5402, 1996.

Zeuner et al., "Reduction of CpG-induced arthritis by suppressive oligodeoxynucleotides," *Arthritis Rheum.* 46(8):2219-2224, 2002.

Zhao et al., "Requirements for effective inhibition of immunostimulatory CpG motifs by neutralizing motifs," *Antisense Nucleic Acid Drug Dev.* 10(5):381-389, 2000.

Zheng et al., "DNA containing CpG motifs induces angiogenesis," *PNAS* 99(13):8944-8949, 2002.

Iwakura et al., "The Development of Autoimmune Inflammatory Arthropathy in Mice Transgenic for the Human T Cell Leukemia Virus Type-1 *env-pX* Region is not Dependent on H-2 Haplotypes and Modified by the Expression Levels of Fas Antigen," *J. Immunology* 161:6592-6598, 1988.

Krieg et al., "Sequence Motifs in Adenoviral DNA Block Immune Activation by Stimulatory CpG Motifs," *Proc. Natl. Acad. Sci. USA* 95:12631-12636 (1998).

Schwartz, CpG Motifs in Bacterial DNA Cause Inflammation in the Lower Respiratory Tract, *J. Clin. Invest.* 100:68-73 (1997).

Schwartz, "Bacterial DNA or Oligonucleotides Containing Unmethylated CpG Motifs Can Minimize Lipopolysaccharide-Induced Inflammation in the Lower Respiratory Tract Through an IL-12-Dependent Pathway," *J. Immunol.* 163:224-231 (1999).

* cited by examiner

US 8,043,622 B2

METHOD OF TREATING INFLAMMATORY LUNG DISEASE WITH SUPPRESSORS OF CPG OLIGONUCLEOTIDES

PRIORITY CLAIM

This application claims the benefit of U.S. Provisional Application No. 60/417,263 filed Oct. 8, 2002, which is incorporated by reference in its entirety.

FIELD OF THE DISCLOSURE

The present disclosure relates to the field of inflammatory lung disease, specifically to the use of oligodeoxynucleotides that suppress an immune response to CpG oligodeoxynucleotides to prevent or treat inflammatory lung disease.

BACKGROUND

Lung disease is the number three killer in America, responsible for one in seven deaths, and lung disease and other breathing problems are the number one killer of babies younger than one year old. Today, more than 30 million Americans are living with chronic inflammatory lung diseases such as emphysema and chronic bronchitis. In addition, approximately 150,000 Americans are affected by acute respiratory distress syndrome (ARDS) each year.

Many lung diseases are associated with lung inflammation. For example, ARDS involves the rapid onset of progressive malfunction of the lungs, and is usually associated with the malfunction of other organs due to the inability to take up oxygen. The condition is associated with extensive lung inflammation and small blood vessel injury in all affected organs. ARDS is commonly precipitated by trauma, sepsis (systemic infection), diffuse pneumonia, and shock. It also may be associated with extensive surgery, and certain blood abnormalities. In many cases of ARDS and other inflammatory lung diseases, the inflammatory response that accompanies the underlying disease state is much more dangerous than the underlying infection or trauma.

Many approaches to the prevention and management of ARDS have been unsuccessful or inconclusive. Treatments that have not improved outcome or prevented ARDS include monoclonal antibody to endotoxin, monoclonal antibody to tumor necrosis factor, interleukin-1 receptor antagonist, prophylactic (early) positive end-expiratory pressure (PEEP), extracorporeal membrane oxygenation and extracorporeal $CO_2$ removal, IV albumin, volume expansion and cardiotonic drugs to increase systemic $O_2$ delivery, corticosteroids in early ARDS, parenteral ibuprofen to inhibit cyclooxygenase, prostaglandin E1, and pentoxifylline.

Other common treatments for ARDS are also problematic. For example, there are safety and toxicity concerns regarding the use of inhaled NO. Inhaling very high levels of NO (5,000 to 20,000 ppm) can be lethal, causing a severe and acute accumulation of fluid in the lungs (pulmonary edema) and methomoglobinemia. Although OSHA has set the safety limit for $NO_2$ at 5 ppm, some investigators have found that prolonged exposure to even 2 ppm of $NO_2$ can be injurious to the lungs. Corticosteroids are of no proven benefit in acute ARDS, although anecdotal reports suggest benefit in some subjects with ARDS in the late fibroproliferative phase, which may develop after 7 to 10 days of mechanical ventilation. Mechanical ventilation, itself, carries risks, as well. For instance, tension pneumothorax is associated with the use of positive pressure ventilation (PPV) and PEEP, and may occur suddenly.

In view of the above, there exists a need for new therapies to treat inflammatory lung disease, particularly agents that suppress the inflammation associated with pneumonia, ARDS, respiratory distress of prematurity, chronic bronchitis, chronic obstructive pulmonary disease (COPD), cystic fibrosis, pulmonary fibrosis, and pulmonary sarcoidosis.

BRIEF SUMMARY OF SPECIFIC EMBODIMENTS

Methods are disclosed herein for using G-tetrad-forming, suppressive oligodeoxynucleotides to suppress lung inflammation. These suppressive oligodeoxynucleotides are of use in inhibiting, preventing and/or treating inflammatory lung diseases, such as, but not limited to, pneumonia, ARDS, respiratory distress of prematurity, chronic bronchitis, COPD, cystic fibrosis, pulmonary fibrosis, and pulmonary sarcoidosis. The suppressive oligodeoxynucleotides can be administered locally, such as, but not limited to, administration by inhalation, or can be administered systemically.

In one embodiment, the disclosed method includes administering a therapeutically effective amount of a suppressive oligodeoxynucleotide (ODN) to a subject having or at risk of developing an inflammatory lung disease. The suppressive ODN is at least about 8 nucleotides in length, forms a G-tetrad, has a circular dichroism (CD) value of greater than about 2.9, and has at least two guanosines. Administration of the suppressive ODN treats or prevents the inflammatory lung disease.

In another embodiment, the disclosed method includes treating or inhibiting acute respiratory distress syndrome in a subject. The method includes locally administering a therapeutically effective amount of a suppressive ODN to a subject having or at risk of developing inflammatory lung disease. The suppressive ODN is at least about 10 nucleotides in length, forms a G-tetrad, and has a CD value of greater than about 3.0. Administration of the suppressive ODN treats or prevents the acute respiratory distress syndrome.

In yet another embodiment, the disclosed method includes reducing the production of a cytokine or chemokine in a cell. In this embodiment, the cell is contacted with a suppressive ODN that is at least about 8 nucleotides in length, forms a G-tetrad, has a CD value of greater than about 2.9, and has at least two guanosines. Contacting the cell with the suppressive ODN thereby reduces the production of the cytokine or chemokine in the cell.

Further embodiments are methods of reducing the production of a cytokine or chemokine in a subject, which include administering to the subject a suppressive ODN. The suppressive ODN is at least about 8 nucleotides in length, forms a G-tetrad, has a CD value of greater than about 2.9, and has at least two guanosines. Administration of the ODN thereby reduces the production of a cytokine or chemokine in the subject.

In yet other embodiments, the disclosed method includes reducing the infiltration of neutrophils in a tissue in a subject. The method includes administering to the subject a suppressive ODN that is at least about 8 nucleotides in length, forms a G-tetrad, has a CD value of greater than about 2.9, and has at least two guanosines. Administration of the ODN reduces the infiltration of neutrophils in the tissue.

BRIEF DESCRIPTION OF THE FIGURES

FIG. 1A is a diagram of the structure of an individual G-tetrad that shows the Hoogsteen base pairing. $M^+$ represents a monovalent cation such as K⁺ or Na⁺ and dR is the sugar-phosphate backbone. FIG. 1B is a schematic representation showing the possible folded intramolecular quadruplex structure. FIG. 1C is a schematic showing the GG-base pair formed by means of Hoogsteen hydrogen bonds. FIG. 1D is a schematic of an intramolecular hairpin.

BRIEF DESCRIPTION OF THE SEQUENCE LISTING

Figure 1:
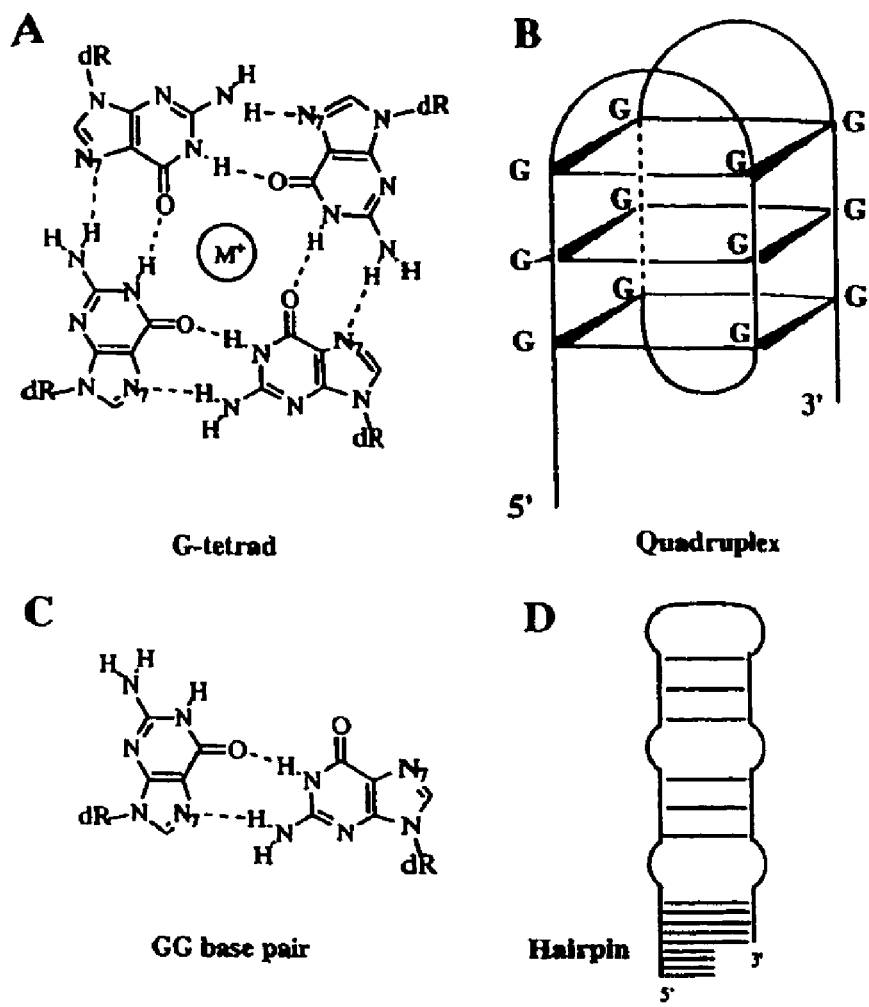
FIG. 1: is a set of diagrams of the structure of a G-tetrad.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-25 are suppressive ODN sequences.
SEQ ID NOs: 26 and 28-30 are control ODN sequences.
SEQ ID NO: 27 is an immunostimulatory CpG sequence.
SEQ ID NOs: 31 and 32 are TNFα-specific primers.
SEQ ID NOs: 33 and 34 are MIP-2-specific primers.
SEQ ID NOs: 35 and 36 are β-actin-specific primers.

DETAILED DESCRIPTION OF SEVERAL EMBODIMENTS

I. Abbreviations

| | |
|---|---|
| A: | adenine |
| Ab: | antibody |
| ALI: | acute lung injury |
| ARDS: | acute respiratory distress syndrome |
| BAL: | bronchoalveolar lavage |
| C: | cytosine |
| CD: | circular dichroism |
| CpG ODN: | an oligodeoxynucleotide including a CpG motif. |
| COPD: | chronic obstructive pulmonary disease |
| DC: | dendritic cell |
| FCS: | fetal calf serum |
| FEF 25-75: | forced expiratory flow determined over the midportion of a forced exhalation |
| FEV1: | forced expired volume in one second |
| FVC: | forced vital capacity |
| G: | guanine |
| h: | hour |
| IL-6: | interleukin 6 |
| KC: | keratinocyte-derived cytokine |
| MIP-2: | macrophage inflammatory protein 2 |
| μg: | microgram |
| mm: | millimeter |
| mRNA: | messenger ribonucleic acid. |
| ODN: | oligodeoxynucleotide |
| Pu: | purine |
| Py: | pyrimidine |
| RDS: | respiratory distress syndrome |
| s.c.: | subcutaneous |
| SPF: | specific pathogen-free |
| T: | thymine |
| TNFα: | tumor necrosis factor alpha |

II. Terms

Unless otherwise noted, technical terms are used according to conventional usage. Definitions of common terms in molecular biology may be found in Benjamin Lewin, *Genes V*, published by Oxford University Press, 1994 (ISN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Acute respiratory distress syndrome (ARDS): A condition characterized by acute hypoxemia respiratory failure due to pulmonary edema (reviewed in Honing, E. G., and Ingram, R. H., Jr., in: *Harrison's Principles of Internal Medicine,* 14th Edition, A. S. Fauci, et al. (eds.), McGraw-Hill, N.Y., pp. 1483-1486, 1998; and Goodman, R. B., et al., *Am J. Respir. Crit. Care Med.* 154:602-11, 1996). ARDS represents a spectrum of responses to acute lung injury (ALI); these responses occur as complications of a more widespread systemic response to acute inflammation or injury. ALI develops rapidly after a predisposing condition triggers a systemic inflammatory response, and is most strongly associated with conditions that produce direct alveolar injury or direct injury via the pulmonary capillary bed, such as aspiration, diffuse infection, toxic inhalation, direct injury to the alveolar epithelium, or sepsis syndrome. ALI is the consequence of unregulated overexpression of usual systemic inflammatory responses to infection and/or injury. Injury involves the alveolar epithelium and the pulmonary capillary endothelium, and results in a complex cascade of events. Injury is produced by cellular events associated with neutrophils, macrophages, monocytes, and lymphocytes producing various cytokines, in turn producing cellular activation, chemotaxis, and adhesion.

Animal: Living multi-cellular vertebrate organisms, a category that includes, for example, mammals and birds. The term mammal includes both human and non-human mammals. Similarly, the term "subject" includes both human and veterinary subjects. Therefore, the general term "subject" is understood to include all animals, including, but not limited to, humans, or veterinary subjects, such as other primates, dogs, cats, horses, and cows.

Anti-Inflammatory Agent: Any of various medications that decrease the signs and symptoms (for example, pain, swelling, or shortness of breath) of inflammation. Corticosteroids are exemplary potent anti-inflammatory medications. Non-steroidal anti-inflammatory agents are also effective exemplary anti-inflammatory agents and do not have the side effects that can be associated with steroid medications.

Bronchodilator: An antispasmodic or other agent that dilates a bronchus or bronchiole. Bronchodilators relax the smooth muscles of the airways, allowing the airway to dilate. Bronchodilator medicines do not counteract inflammation.

CD value: The formation of G-tetrads yields a complex with different physical properties than the individual oligonucleotides. Spectroscopically, this is manifested by an increase in circular dichroism (CD), and an increase in peak absorbance to the 260-280 nm wavelength owing to the formation of secondary structures. Thus, a convenient method for identifying oligonucleotides that form G-tetrads is to study their CD values. An increase in peak ellipticity values to greater than 2.0 is typical of a G-tetrad forming oligonucleotide. The higher the ellipticity value, the greater the tetrad-forming capacity of the oligonucleotide.

Chemokine: A type of cytokine (a soluble molecule that a cell produces to control reactions between other cells) that specifically alters the behavior of leukocytes (white blood cells). Examples include, but are not limited to, interleukin 8 (IL-8), platelet factor 4, melanoma growth stimulatory protein, etc.

Chronic Bronchitis: A long-standing inflammation of the airways that produces a lot of mucus, causing wheezing and infections. It is considered chronic if a subject has coughing and mucus on a regular basis for at least three months a year and for two years in a row.

Chronic Obstructive Pulmonary Disease (COPD): COPD refers mainly to two closely related respiratory disorders that cause gradual loss of pulmonary function: chronic bronchitis and emphysema associated with airflow obstruction. A subject with COPD sometimes has both chronic bronchitis and emphysema, or may just have one of these diseases. Chronic bronchitis is a long-standing inflammation of the airways that produces a lot of mucus, causing wheezing and infections. It is considered chronic if a subject has coughing and mucus on a regular basis for at least three months a year and for two years in a row. Emphysema is a disease that destroys the alveolae and/or bronchae. Simply put, the lungs lose elasticity. This causes the air sacs to become enlarged, thus making breathing difficult.

In the beginning stages of COPD, a subject may have only a mild shortness of breath and occasional coughing spells. Initial symptoms can include a general feeling of illness, increasing shortness of breath, coughing, and wheezing. But, as the disease progresses, symptoms become increasingly more severe.

The overwhelming cause of COPD is smoking. Approximately 90% of COPD subjects have a history of smoking. In addition, untreated or under-treated asthma may lead to irreversible lung damage. These subjects may have symptoms similar to COPD.

Cystic Fibrosis: A disease that most commonly affects the lungs and digestive systems, especially the pancreas. It causes the exocrine glands, which produce mucus and sweat, to produce abnormal secretions. Cystic fibrosis causes the cells in the lung tissue to produce an abnormal amount of thick, sticky mucus that clogs the airways of the lungs, resulting in pulmonary obstructions and life-threatening bacterial infections.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor α (TNFα), interleukin 6 (IL-6), interleukin 10 (IL-10), interleukin 12 (IL-12), macrophage inflammatory protein 2 (MIP-2), KC, and interferon-γ (INF-γ).

Enzyme: Any of numerous proteins or conjugated proteins produced by living organisms and functioning as biochemical catalysts.

Expectorant: A drug or chemical substance that induces the ejection of mucus, phlegm, and other fluids from the lungs and air passages, for example by coughing.

Expiratory Flow Rate: The rate at which air is expelled from the lungs during exhalation. A subject's maximum expiratory flow is measured by a simple pulmonary test; in performing the test, a subject first takes as deep a breath as possible, then exhales as rapidly and as completely as possible into a machine known as a spirometer, which measures the rate of exhalation. Forced expiratory flow 25-75 (FEF 25-75) is a measurement of the forced expiratory flow determined over the midportion of a forced exhalation. An increase in the forced expiratory flow (FEF) or FEF 25-75 reflects a decrease in bronchoconstriction and an improvement in pulmonary function.

Forced Expiratory Volume (FEV): The forced expiratory volume is the volume of air resulting from the forced expiratory flow test in which a subject first inspires maximally to the total lung capacity, then exhales as rapidly and as completely as possible. The forced expired volume in one second (FEV1) represents the maximum expiratory air volume a subject can produce during a one-second interval. An increase in FEV or FEV1 reflects a decrease in bronchoconstriction and an improvement in pulmonary function.

Forced Vital Capacity (FVC): The volume of air resulting from the forced expiratory flow test in which a subject first inspires maximally to the total lung capacity, then exhales as rapidly and as completely as possible. An increase in FVC reflects a decrease in bronchoconstriction and an improvement in pulmonary function.

G-tetrad: G-tetrads are G-rich DNA segments that can accommodate complex secondary and/or tertiary structures (see FIG. 1). A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of contiguous Gs, and the higher the G content of the ODN, the higher the likelihood of G-tetrad formation, as reflected by higher CD or ellipticity values.

Oligonucleotides that form G-tetrads can also form higher-level aggregates that are more easily recognized and taken up by immune cells, for example, through scavenger receptors or by nucleolin.

Guanosine-rich sequence: A hexameric region of a nucleotide sequence in which >50% of the bases are Gs.

Immune response: A response of a cell of the immune system, such as a B cell or T cell to a stimulus. In one embodiment, the response is an inflammatory response.

Immunostimulatory CpG motifs: Immunostimulatory sequences that trigger macrophages, monocytes and lymphocytes to produce a variety of pro-inflammatory cytokines and chemokines. CpG motifs are found in bacterial DNA. The innate immune response elicited by CpG DNA reduces host susceptibility to infectious pathogens, and can also trigger detrimental inflammatory reactions. Immunostimulatory CpG motifs are found in "D" and "K" type ODNs (see, U.S. patent application Ser. No. 10/194,035, filed Jul. 12, 2002).

Infiltration: The diffusion or accumulation of a substance, such as a neutrophil, in a tissue or cell.

Inflammatory lung disease: Many disease of the lung are associated with lung inflammation. For example, ARDS is the rapid onset of progressive malfunction of the lungs, and is usually associated with the malfunction of other organs due to the inability to take up oxygen. The condition is associated with extensive lung inflammation and small blood vessel injury in all affected organs. ARDS is commonly precipitated by trauma, sepsis (systemic infection), diffuse pneumonia and shock. It may be associated with extensive surgery, and certain blood abnormalities.

In many inflammatory lung diseases, the inflammatory response that accompanies the underlying disease state is much more dangerous than the underlying infection or trauma. Inflammatory lung diseases can include, but are not limited to pneumonia, ARDS, respiratory distress of prematurity, chronic bronchitis, COPD, cystic fibrosis, pulmonary fibrosis, and pulmonary sarcoidosis. In contrast, inflammatory lung diseases of the present disclosure do not include LPS-induced lung conditions or allergic lung conditions, such as asthma.

Inflammatory response: An accumulation of white blood cells, either systemically or locally at the site of inflammation. The inflammatory response may be measured by many methods well known in the art, such as the number of white blood cells (WBC), the number of polymorphonuclear neutophils (PMN), a measure of the degree of PMN activation, such as luminal enhanced-chemiluminescence, or a measure of the amount of cytokines present.

Inspiratory Flow Rate: The rate at which air travels into the lungs during inspiration. Inspiratory flow is measured by a simple pulmonary test; in performing the test the subject takes as deep and rapid a breath as possible from a machine known as a spirometer, which measures the rate of inspiration. An increase in inspiratory flow rate reflects a decrease in bronchoconstriction and an improvement in pulmonary function.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are five main types of white blood cells, subdivided into two main groups: polymorphonuclear leukocytes (neutrophils, eosinophils, basophils) and mononuclear leukocytes (monocytes and lymphocytes). When an infection is present, the production of leukocytes increases.

Leukotriene Antagonist/Leukotriene Formation Inhibitor: Drugs that block the effects of leukotrienes (leukotriene antagonists) or inhibit the formation of leukotrienes (leukotriene formation inhibitors). Leukotrienes are substances that are associated with an allergic response and inflammation. In the airways, they cause bronchial or alveolar narrowing and increase secretions. Drugs can interfere with leukotriene action by inhibiting their synthesis (for example, zileuton, ZYFLO, Abbott Laboratories) or blocking the receptor to which they bind (for example, monteleukast, SINGULAIR, Merck and Company, and others).

Lung Volume: The maximum volume the lungs can hold.

Macrophage: A monocyte that has left the circulation and settled and matured in a tissue. Macrophages are found in large quantities in the spleen, lymph nodes, alveoli, and tonsils. About 50% of all macrophages are found in the liver as Kupffer cells. They are also present in the brain as microglia, in the skin as Langerhans cells, in bone as osteoclasts, as well as in seous cavities and breast and placental tissue.

Along with neutrophils, macrophages are the major phagocytic cells of the immune system. They have the ability to recognize and ingest foreign antigens through receptors on the surface of their cell membranes; these antigens are then destroyed by lysosomes. Their placement in the peripheral lymphoid tissues enables macrophages to serve as the major scavengers of the blood, clearing it of abnormal or old cells and cellular debris as well as pathogenic organisms. Macrophages also serve a vital role by processing antigens and presenting them to T cells, activating the specific immune response. They also release many chemical mediators that are involved in the body's defenses, including interleukin-1.

Mast Cell Stabilizer: A class of anti-inflammatory agents that work by preventing the release of substances in the body that cause inflammation. This is done by controlling the release of histamine from a white blood cells called mast cells. Examples include cromolyn and nedocromil.

Neutrophil: A white blood cell, found in abundance in the human body, that phagocytoses invading bacterial cells. As with all leukocytes, neutrophils are produced and partially matured in the bone marrow. They are very short-lived, lasting from a few hours to a few days. They are released in a form known as a "band" neutrophil which matures into a "segmented" neutrophil in the blood. During acute bodily stress, even less mature forms, known as "myelocytes", are released from the marrow. A high neutrophil count in the blood, especially in the presence of myelocytes, is an indicator of bodily stress. For example, cigarette smoking, obesity, and infection, such as lung infection, increase the neutrophil count.

Neutrophils locate damage sites through messenger proteins called chemokines. Macrophages, which are usually the first leukocytes to arrive at the scene of an attack, release these chemokines, which causes the inside layer of the surrounding blood vessels (the endothelium) to produce adhesion proteins that specifically bind to receptors on the neutrophils. Once there, the neutrophils migrate to the damage site by following the gradient of chemokines.

Neutrophils contain supplies of highly toxic substances including peroxidases, hydrolytic enzymes, and defensins (antibiotic-like proteins), which they keep in "cytotoxic granules". When they engulf invading cells, they release these granules, poisoning both the invader and the neutrophil.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e., molecules comprising a sugar (e.g., ribose or deoxyribose) linked to a phosphate group and to an exchangeable organic base, which is either a substituted pyrimidine (Py) (e.g., cytosine (C), thymine (T) or uracil (U)) or a substituted purine (Pu) (e.g., adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (i.e., an oligonucleotide minus the phosphate) and any other organic base polymer. Oligonucleotides can be obtained from existing nucleic acid sources (e.g., genomic or cDNA), but are preferably synthetic (i.e., produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "oligonucleotide delivery complex" is an oligonucleotide associated with (e.g., ionically or covalently bound to; or encapsulated within) a targeting means (e.g., a molecule that results in a higher affinity binding to a target cell (e.g., B-cell or natural killer (NK) cell) surface and/or increased cellular uptake by target cells). Examples of oligonucleotide delivery complexes include oligonucleotides associated with: a sterol (e.g., cholesterol), a lipid (e.g., cationic lipid, virosome or liposome), or a target cell specific binding agent (e.g., a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001)

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intraarticularly, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject. Pharmaceutical agents include, but are not limited to, anti-infective agents, anti-inflammatory agents, bronchodilators, enzymes, expectorants, leukotriene antagonists, leukotriene formation inhibitors, and mast cell stabilizers.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the suppressive ODNs herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pneumonia: A disease of the lungs characterized by inflammation and consolidation followed by resolution and caused by infection from viruses, fungi, or physical and chemical irritants or bacteria including: *Pneumonococcus, Streptococcus, Hemolyticus, Staphylococcus, Friedländer's bacillus*, and *influenza bacillus*. Symptoms include high fever, chest pain, difficulty breathing, coughing and sputum.

Preventing or treating a disease: Inhibiting a disease refers to inhibiting the full development of a disease, for example in a person who is at risk for a disease such as an inflammatory lung disease. An example of a person at risk for an inflammatory lung disease is someone with a history of inflammatory lung diseases in the family, or who has been exposed to factors that predispose the subject to a condition, such as COPD or emphysema. Inhibiting a disease process includes preventing the development of the disease. "Treatment" refers to a therapeutic intervention that ameliorates a sign or symptom of a disease or pathological condition after it has begun to develop.

Pulmonary Fibrosis: Pulmonary Fibrosis or Idiopathic Pulmonary Fibrosis (IPF) is a disease of inflammation that results in scarring, or fibrosis, of the lungs. In time, this fibrosis can build up to the point where the lungs are unable to provide oxygen to the tissues of the body. The word "idiopathic" is used to describe the disease because the cause of IPF is unknown. Currently, it is believed that IPF may result from either an autoimmune disorder, or the after effects of an infection, most likely a virus.

Whatever the trigger is for IPF, it appears to set off a series of events in which the inflammation and immune activity in the lungs (and, eventually, the fibrosis processes too) become uncontrollable. In a few cases, heredity appears to play a part, possibly making some individuals more likely than others to get IPF. In studies of subjects with IPF, the average survival rate has been found to be 4 to 6 years after diagnosis. Those who develop IPF at a young age seem to have a longer survival.

Pulmonary Sarcoidosis: Sarcoidosis is a rare disease that results from inflammation. Ninety percent of the cases of sarcoidosis are found in the lungs, but it can occur in almost any organ. It causes small lumps, or granulomas, which generally heal and disappear on their own. However, for those granulomas that do not heal, the tissue can remain inflamed and become scarred, or fibrotic.

Pulmonary sarcoidosis can develop into pulmonary fibrosis, which distorts the structure of the lungs and can interfere with breathing. Bronchiectasis, a lung disease in which pockets form in the air tubes of the lung and become sites for infection, can also occur.

Respiratory Distress of Prematurity: Also called respiratory distress syndrome (RDS), results from a lack of pulmonary surfactant, a molecular substance that helps the lung's alveoli (air sacs) do their job of extracting carbon dioxide from the blood and replacing it with oxygen. The surfactant prevents the lung's alveoli from collapsing and helps keep them properly inflated by reducing their surface tension. The absence of surfactant prevents the alveoli from functioning properly.

Suppressive ODN: DNA molecules of at least eight nucleotides in length, wherein the oligodeoxynucleotide forms a G-tetrad, and has a CD value of greater than about 2.9. In a suppressive ODN the number of guanosines is at least two. In one embodiment, a suppressive ODN inhibits inflammation, for example lung inflammation.

Therapeutic agent: Used in a generic sense, it includes treating agents, prophylactic agents, and replacement agents.

Therapeutically effective amount: A quantity of a specified compound or ODN sufficient to achieve a desired effect in a subject being treated. For instance, this can be the amount of a suppressive ODN necessary to suppress CpG-induced immune cell activation in a subject, or a dose sufficient to prevent advancement, or to cause regression of a disease, or which is capable of relieving symptoms caused by a disease, such as pain, lung inflammation, fluid accumulation, or shortness of breath.

A therapeutically effective amount of a suppressive ODN can be administered systemically or locally. In addition, an effective amount of a suppressive ODN can be administered in a single dose, or in several doses, for example daily, during a course of treatment. However, the effective amount of the ODN will be dependent on the preparation applied, the subject being treated, the severity and type of the affliction, and the manner of administration of the compound. For example, a therapeutically effective amount of a suppressive ODN can vary from about 0.01 mg/kg body weight to about 1 g/kg body weight in some specific, non-limiting examples, or from about 0.01 mg/kg to about 60 mg/kg of body weight, based on efficacy.

The suppressive ODNs disclosed herein have equal applications in medical and veterinary settings. Therefore, the general term "subject" is understood to include all animals, including, but not limited to, humans or veterinary subjects, such as other primates, dogs, cats, horses, and cows.

III. Description of Several Embodiments

A. Suppressive Oligodeoxynucleotides and Guanosine-Quadruplexes (G-Tetrads)

The present disclosure relates to the use of a class of DNA motifs that selectively inhibits or suppresses immune activation. Optimal activity is observed using multimers of these motifs, which are rich in G bases and capable of forming G-quadruplexes (G-tetrads). G-tetrads are G-rich DNA segments that can accommodate complex secondary and/or tertiary structures (see FIG. 1). The suppressive ODNs of the disclosure are highly specific (i.e., are neither toxic nor non-specifically immunosuppressive), and are useful for inhibiting an immune response. In one embodiment, a suppressive ODN is of use for blocking immunostimulation caused by CpG motifs in vivo and in vitro.

A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of continuous Gs, and the higher the G content of the ODN, the higher the likelihood of G-tetrad formation, as reflected by higher ellipticity values. Oligonucleotides that form G-tetrads can also form higher-level aggregates that are more easily recognized and taken up by immune cells, for example, through scavenger receptors or by nucleolin.

The formation of G-tetrads yields a complex with different physical properties than the individual oligonucleotides. Spectroscopically, this is manifested by an increase in CD, and an increase in peak absorbance to the 260-280 nm wavelength, owing to the formation of secondary structures. Thus, a convenient method for identifying oligonucleotides that form G-tetrads is to study their CD values. An increase in peak ellipticity values to greater than 2.0 is typical of a G-tetrad forming oligonucleotide. For instance, G-tetrad-forming ODNs can have CD values of 2.2, 2.4, 2.6, 2.8, 3.0, 3.2, 3.5, 4.0, 4.5, 5.0, 5.5, 6.0, 6.5, 7.0, 7.5, 8.0, 8.5, 9.0, or higher. The higher the ellipticity value, the greater the tetrad-forming capacity of the oligonucleotide, so an ODN with a CD value of 8.5 is typically more suppressive than an ODN with a CD value of 2.9.

In some embodiments, the ODN is from about 8 to about 100 nucleotides in length. In particular examples, the ODN is from about 10 to about 30 nucleotides in length. Optionally, the suppressive ODN has multiple guanosine-rich sequences, for example, in certain embodiments the ODN has from about two to about 20 guanosine-rich sequences, or, more particularly, from about two to about four guanosine-rich sequences.

In one embodiment, the suppressive ODNs have a sequence comprising at least one of the human telomerederived TTAGGG suppressive motifs (see Example 1). In some examples, the ODN has at least one TTAGGG motif, and in certain examples, the ODN has multiple TTAGGG motifs. For example, in particular embodiments, the ODN has from about two to about 20 TTAGGG motifs, or from about two to about four TTAGGG motifs. In this embodiment, suppressive ODNs containing multiple TTAGGG repeats are the most suppressive. Single TTAGGG motifs are suppressive only when incorporated into larger ODNs with greater than 10 bases. The TTAGGG motifs may be in either the cis or trans position, i.e., they may be present on the same or on a different strand of DNA than that expressing the stimulatory CpG sequence.

Suppression of CpG-induced immune activation requires a G-tetrad-forming sequence that imposes the two-dimensional structure necessary for G-tetrad formation. Examples of suppressive ODN include, but are not limited to, those shown in Table 1. However, any oligonucleotide capable of forming G-tetrads may be used to suppress CpG DNA-induced immune activation. In particular examples, the ODN has a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 (see Table 1).

Furthermore, in particular embodiments the ODN is modified to prevent degradation. In one embodiment, suppressive ODNs can include modified nucleotides to confer resistance to degradation. Without being bound by theory, modified nucleotides can be included to increase the stability of a suppressive ODN. Thus, because phosphorothioate-modified nucleotides confer resistance to exonuclease digestion, the suppressive ODNs are "stabilized" by incorporating phosphorothioate-modified nucleotides.

TABLE 1

List of suppressive ODNs

| | | | |
|---|---|---|---|
| 1 | A151 | SEQ ID NO: 2 | (TTAGGG)$_4$ (ie-4 repeats of the TTAGGG base sequence) |
| 2 | A152 | SEQ ID NO: 3 | (TTAGGG)$_3$ |
| 3 | A153 | SEQ ID NO: 4 | (TTAGGG)$_2$ |
| 4 | A156 | SEQ ID NO: 5 | (TGGGCGGT)$_3$ |
| 5 | A157 | SEQ ID NO: 6 | (TGGGCGGT)$_2$ |
| 6 | A1 | SEQ ID NO: 7 | TCAACCTTCATTAGGG |
| 7 | A161 | SEQ ID NO: 8 | TTAGGGTTAGGGTCAACCTTCA |
| 8 | A162 | SEQ ID NO: 9 | TCAACCTTCATTAGGGTTAGGG |
| 9 | A163 | SEQ ID NO: 10 | GGGTTAGGGTTATCAACCTTCA |
| 10 | A164 | SEQ ID NO: 11 | TCAACCTTCAGGGTTAGGGTTA |
| 11 | A15 | SEQ ID NO: 12 | GGGTGGGTGGGTATTACCATTA |
| 12 | A16 | SEQ ID NO: 13 | ATTACCATTAGGGTGGGTGGGT |
| 13 | A17 | SEQ ID NO: 14 | TGGGCGGTTCAAGCTTGA |
| 14 | A18 | SEQ ID NO: 15 | TCAAGCTTCATGGGCGGT |
| 15 | A19 | SEQ ID NO: 16 | GGGTGGGTGGGTAGACGTTACC |
| 16 | A20 | SEQ ID NO: 17 | GGGGGGTCAAGCTTCA |
| 17 | A21 | SEQ ID NO: 18 | TCAAGCTTCAGGGGGG |
| 18 | A22 | SEQ ID NO: 19 | GGGGGGTCAACGTTCA |
| 19 | H154 | SEQ ID NO: 1 | CCTCAAGCTTGAGGGG |
| 20 | 1502 | SEQ ID NO: 20 | GAGCAAGCTGGACCTTCCAT |
| 21 | 1502(7DG) | SEQ ID NO: 28 | GAGCAAGCTG*G*ACCTTCCAT |
| 22 | 1502-1555 | SEQ ID NO: 21 | GAGCAAGCTGGTAGACGTTAG |
| 23 | 1502-1555 (7DG) | SEQ ID NO: 29 | GAG*CAAGCTG*GTAGACGTTAG |
| 24 | 1502-1555 (7DG) | SEQ ID NO: 30 | G*AGCAAGCTG*GTAGACGTTAG |
| 25 | 1503 | SEQ ID NO: 22 | GGGCAAGCTGGACCTGGGGG |
| 26 | 1504 | SEQ ID NO: 23 | GGGGAAGCTGGACCTGGGGG |
| 27 | 1505 | SEQ ID NO: 24 | GGGCAAGCTGGACCTTCGGG |
| 28 | 1506 | SEQ ID NO: 25 | GGCAAGCTGGACCTTCGGGGG |

In the table above, G* indicates 7-deazaguanine. Due to the presence of 7-deazaguanine, ODN 21 (SEQ ID NO: 28) is an inactive form of ODN 20 (SEQ ID NO: 20), and ODNs 23 and 24 (SEQ ID NOs: 29 and 30, respectively) are inactive forms of ODN 22 (SEQ ID NO: 21).

In some embodiments, the ODN has a phosphate backbone modification, and in particular examples, the phosphate backbone modification is a phosphorothioate backbone modification. In one embodiment, the guanosine-rich sequence and its immediate flanking regions include phosphodiester rather than phosphorothioate nucleotides. In one specific non-limiting example, the sequence TTAGGG includes phosphodiester bases. In some examples, all of the bases in an ODN are phosphodiester bases. In other examples, the ODN is a phosphorothioate/phosphodiester chimera.

As disclosed herein, any suitable modification can be used to render the ODN resistant to degradation in vivo (e.g., via an exo- or endo-nuclease). In one specific, non-limiting example, a modification that renders the ODN less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

The suppressive ODNs of the disclosure can be synthesized by standard methods well known in the art. Most commonly, synthesis is performed on an oligonucleotide synthesizer using the standard cyanoethyl phosphoramidite chemistry. These include, but are not limited to, phosphodiester, phosphorothioate, peptide nucleic acids, synthetic peptide analogues, and any combination thereof. Those skilled in the art will recognize that any other standard technique may be used to synthesize the suppressive ODN described herein.

In one embodiment, a suppressive ODN is included in a delivery complex. The delivery complex can include the suppressive ODN and a targeting agent. Any suitable targeting agent can be used. For example, in some embodiments, a suppressive ODN is associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of oligodeoxynucleotide delivery complexes include a suppressive ODN associated with a sterol (e.g., cholesterol), a lipid (e.g., a cationic lipid, anionic lipid, virosome or liposome), and a target cell specific binding agent (e.g., a ligand recognized by target cell specific receptor). Without being bound by theory, the complex is sufficiently stable in vivo to prevent significant uncoupling prior to delivery to the target cell. In one embodiment, the delivery complex is cleavable such that the ODN is released in a functional form at the target cells.

B. Pharmaceutical Compositions

The suppressive ODNs described herein may be formulated in a variety of ways depending on the location and type of disease to be treated. Pharmaceutical compositions are thus provided for both local (e.g. inhalational) use and for systemic use. Therefore, the disclosure includes within its scope pharmaceutical compositions comprising at least one suppressive ODN formulated for use in human or veterinary medicine. While the suppressive ODNs will typically be used to treat human subjects they may also be used to treat similar or identical diseases in other vertebrates, such other primates, dogs, cats, horses, and cows.

Pharmaceutical compositions that include at least one suppressive ODN as described herein as an active ingredient, or that include both a suppressive ODN and an additional respiratory agent as active ingredients, may be formulated with an appropriate solid or liquid carrier, depending upon the particular mode of administration chosen. Additional active ingredients include, for example, anti-infective agents, anti-inflammatory agents, bronchodilators, enzymes, expectorants, leukotriene antagonists, leukotriene formation inhibitors, and mast cell stabilizers. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988.

The dosage form of the pharmaceutical composition will be determined by the mode of administration chosen. For instance, in addition to injectable fluids, inhalational and oral formulations can be employed. Inhalational preparations can include aerosols, particulates, and the like. In general, the goal for particle size for inhalation is about 1 μm or less in order that the pharmaceutical reach the alveolar region of the lung for absorption. Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intraperitoneal, intramuscular, intraperitoneal, intrasternal, or intraarticular injection or infusion, or by sublingual, oral, topical, intranasal, or transmucosal administration, or by pulmonary inhalation. When suppressive ODNs are provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

Suppressive ODNs are also suitably administered by sustained-release systems. Suitable examples of sustained-release suppressive ODNs include suitable polymeric materials (such as, for example, semi-permeable polymer matrices in the form of shaped articles, e.g., films, or microcapsules), suitable hydrophobic materials (such as, for example, an emulsion in an acceptable oil) or ion exchange resins, and sparingly soluble derivatives (such as, for example, a sparingly soluble salt). Sustained-release suppressive ODNs may be administered orally, rectally, parenterally, intracistemally, intravaginally, intraperitoneally, topically (as by powders, ointments, gels, drops or transdermal patch), bucally, or as an oral or nasal spray.

Preparations for administration can be suitably formulated to give controlled release of suppressive ODNs. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate.

For administration by inhalation, the compounds can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Pharmaceutical compositions that comprise a suppressive ODN as described herein as an active ingredient will normally be formulated with an appropriate solid or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, suppressive ODNs can be formulated generally by mixing them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the suppressive ODNs each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise a suppressive ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of suppressive ODN will be dependent on the ODN utilized, the subject being treated, the severity and type of the affliction, and the manner of administration. For example, a therapeutically effective amount of suppressive ODN can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound (such as the suppressive ODN utilized), the age, weight, sex and physiological condition of the subject.

Therapeutically effective amounts of a suppressive ODN for use in reducing lung inflammation are those that reduce inflammation or improve breathing or oxygenation to a desired level. As will be recognized by those in the field, an effective amount of therapeutic agent will vary with many factors including the potency of the particular ODN, the age and weight of the patient, the patient's physical condition, the oxygenation level, and other factors.

Administration may begin whenever the suppression of lung inflammation is desired, for example, at the first sign of symptoms of an inflammatory lung disease or shortly after diagnosis of pneumonia, ARDS, respiratory distress of prematurity, chronic bronchitis, COPD, cystic fibrosis, pulmonary fibrosis, or pulmonary sarcoidosis. Alternatively, administration may begin whenever decreased neutrophil infiltration or cytokine production is desired in the lungs, or at the first sign of increased neutrophil infiltration or increased cytokine production.

C. Therapeutic Uses

A method is disclosed herein for treating or inhibiting inflammatory lung disease in a subject. Inflammatory lung diseases include, but are not limited to pneumonia, ARDS, respiratory distress of prematurity, chronic bronchitis, COPD, cystic fibrosis, pulmonary fibrosis, and pulmonary sarcoidosis. The method includes administering a therapeutically effective amount of the suppressive ODN to a subject having or at risk of developing inflammatory lung disease, thereby treating or inhibiting the inflammatory lung disease. In one embodiment, the suppressive ODN can be administered locally, such as by inhalation. In another embodiment, the suppressive ODN is administered systemically, such as by intravenous injection.

In order to treat or prevent an inflammatory lung disease, a therapeutically effective amount of a suppressive ODN (see above) is administered to the subject. Combinations of these suppressive ODN are also of use. Thus, in one embodiment, more than one suppressive ODN, each with a different nucleic acids sequence, are administered to the subject. In several specific, non-limiting examples, at least two, at least three, or at least four suppressive ODNs are administered to the subject.

In another embodiment an additional anti-infective agent, anti-inflammatory agent, bronchodilator, enzyme, expectorant, leukotriene antagonist, leukotriene formation inhibitor, or mast cell stabilizer is administered in conjunction with a suppressive ODN. The administration of the additional agent and the suppressive ODN can be sequential or simultaneous.

An effective amount of a suppressive ODN can be administered in a single dose, or in multiple doses, for example daily, during a course of treatment. In one embodiment, a therapeutically effective amount of a suppressive ODN is administered as a single pulse dose, as a bolus dose, or as pulse doses administered over time. Thus, in pulse doses, a bolus administration of a suppressive ODN is provided, followed by a time period wherein no suppressive ODN is administered to the subject, followed by a second bolus administration. In specific, non-limiting examples, pulse doses of a suppressive ODN are administered during the course of a day, during the course of a week, or during the course of a month.

Thus, the suppressive ODNs disclosed herein may be administered to a subject for the treatment of inflammatory lung disease in that individual. ODN administration can be systemic or local. Local administration of the ODN is performed by methods well known to those skilled in the art. By way of example, one method of administration to the lungs of an individual is by inhalation through the use of a nebulizer or inhaler. For example, the ODN is formulated in an aerosol or particulate and drawn into the lungs using a standard nebulizer well known to those skilled in the art.

In other embodiments, the administration of the suppressive ODN is systemic. Oral, intravenous, intraarterial, subcutaneous, intraperitoneal, intramuscular, and even rectal administration is contemplated.

The effectiveness of treatment with a suppressive ODN can be measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, and lung volume. A statistically significant increase, as determined by mathematical formulas well known to those skilled in the art, in one or more of these parameters indicates efficacy of the suppressive ODN treatment.

The methods of measuring pulmonary function most commonly employed in clinical practice involve timed measurement of inspiratory and expiratory maneuvers to measure specific parameters. For example, FVC measures the total volume in liters exhaled by a patient forcefully from a deep initial inspiration. This parameter, when evaluated in conjunction with the FEV 1, allows bronchoconstriction to be quantitatively evaluated. A statistically significant increase, as determined by mathematical formulas well known to those skilled in the art, in FVC or FEV1 reflects a decrease in bronchoconstriction, and indicates that suppressive ODN therapy is effective.

A problem with forced vital capacity determination is that the forced vital capacity maneuver (i.e., forced exhalation from maximum inspiration to maximum expiration) is largely technique dependent. In other words, a given subject may produce different FVC values during a sequence of consecutive FVC maneuvers. The FEF 25-75 or forced expiratory flow determined over the midportion of a forced exhalation maneuver tends to be less technique dependent than the FVC. Similarly, the FEV1 tends to be less technique-dependent than FVC. Thus, a statistically significant increase, as determined by mathematical formulas well known to those skilled in the art, in the FEF 25-75 or FEV1 reflects a decrease in bronchoconstriction, and indicates that suppressive ODN therapy is effective.

In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest airflow rate in liters per minute during a forced maximal exhalation, is well correlated with overall pulmonary function in a patient with asthma and other respiratory diseases. Thus, a statistically significant increase, as determined by mathematical formulas well known to those skilled in the art, in the peak expiratory flow following administration of a suppressive ODNs indicates that the therapy is effective.

Further methods disclosed herein are methods of decreasing cytokine or chemokine production in a cell. The methods include contacting the cell with a suppressive oligodeoxynucleotide as described above, thereby decreasing cytokine or chemokine production in the cell. In some embodiments, the cell is a macrophage.

Methods are also disclosed for decreasing cytokine or chemokine production in a subject. The methods include administering to the subject a suppressive oligodeoxynucleotide as described above, thereby reducing the production of cytokines or chemokines in the subject. Cytokine levels in body fluids or cell samples are determined by conventional methods known by those of skill in the art. For example, cytokine concentrations in cell culture supernatants and BAL fluid can be measured as recommended by the manufacturer of ELISA kits (R&D systems, Minneapolis, Minn.).

Also disclosed are methods of reducing the infiltration of neutrophils in a subject. Methods of measuring neutrophil infiltration are well known to those of skill in the art. For example, measurement of myeloperoxidase activity is often used as a marker of neutrophils infiltration into tissues. Myeloperoxidase is a hemoprotein present in azurophilic granules of polymorphonuclear leukocytes and monocytes. It catalyzes the oxidation of halide ions to their respective hypohalous acids, which are used for microbial killing by phagocytic cells. Thus, a decrease in myeloperoxidase activity in a tissue reflects decreased neutrophil infiltration, and can serve as a measure of suppressive ODN efficacy.

The subject matter of the present disclosure is further illustrated by the following non-limiting Examples.

EXAMPLES

Example 1

General Methods

Reagents

Endotoxin-free oligodeoxynucleotides were synthesized at the CBER core facility. Sequences of the ODN used were (5'-3'):

```
CpG ODN 1555:
GCTAGACGTTAGCGT,         (SEQ ID NO: 27)

neutral ODN 1612:
GCTAGATGTTAGCGT,         (SEQ ID NO: 26)

suppressive ODN H154:
CCTCAAGCTTGAGGGG.        (SEQ ID NO: 1)
```

*E. coli* and calf thymus DNA were purchased from Sigma (St. Louis, Mo.) and re-purified by extraction with phenol/chloroform/isomyl alcohol, 25:24:1 and ethanol precipitation followed by passage through an EndoFree plasmid purification column (Quiagen Inc., Chatsworth, Calif.). Endotoxin levels were below the detection limit of 0.02 U/µl as determined using the Limulus Amebocyte Lysate analysis kit (QCL-1000, BioWhittaker, Walkersville, Md.).

Cell Culture

The RAW 264.7 murine macrophage cell line (American Type Culture Collection, Rockville Md.), was cultured in Dulbecco's modified Eagle's medium (Life Technologies Inc., Gaithersburg, Md.) supplemented with 10% fetal calf serum, 50 mg/ml of penicillin, 50 mg/ml of streptomycin, 2 mM L-glutamine, 10 mM HEPES, 0.11 mg/ml sodium pyruvate, and 0.5 mM β-mercaptoethanol. The cells were maintained at 37° C. in 5% $CO_2$.

For in vitro experiments, $2\times10^5$ RAW cells/well were incubated with 1 µM of ODN for 24 h. Culture supernatants were assayed for TNFα, MIP-2, IL-6 and KC by ELISA.

Animal Procedures

Eight to twelve week old BALB/c mice (Jackson Laboratories, Bar Harbor, Me.) were maintained in an SPF facility.

Animals were anesthetized with inhaled isoflurane, and ODNs administered intratracheally using a sterile, blunt, fine bore needle. At various times post treatment, animals were sacrificed. The trachea was exposed by a midline incision, an 18-gauge catheter inserted, and the lungs lavaged 4 times with 1 ml aliquots of PBS. The BAL fluid was pooled, centrifuged at 500×g for 10 minutes at 4° C. Supernatants were stored at −70° C. until assay. Cell pellets were resuspended in PBS, counted, spun onto a glass slide (Cytospin 2; Shandon, Pittsburgh, Pa.), and individual cell types quantitated following staining with Diff-Quik (Dade Behring Inc., Newark, Del.).

Cytokine ELISAs

Cytokine concentrations in cell culture supernatants and BAL fluid were measured as recommended by the manufacturer of ELISA kits (R&D systems, Minneapolis, Minn.).

RT-PCR tRNA was prepared from cells stimulated in vitro with 1 μM of ODN for 24 h using TRIzol reagent (Life Technologies Inc.). Five μg of tRNA was reverse transcribed for 1 h at 42° C. in first strand buffer (50 μM Tris-HCl, pH 7.5, 75 mM KCl, and 2.5 mM MgCl2) containing 0.5 μg of oligo-(dT)12-18, 200 U reverse transcriptase, 0.5 mM dNTP, and 10 mM DTT. One μl of the cDNA synthesis was PCR amplified for 25 cycles using the following primer pairs (5'-3'):

```
TNFα:
ATGAGCACAGAAAGCATGATC         (SEQ ID NO: 31)
and

TACAGGCTTGTCACTCGAATT         (257 bp;
                               SEQ ID NO: 32)

MIP-2:
ATGGCCCCTCCCACCTGCCGGCTCC     (SEQ ID NO: 33)
and

TCAGTTAGCCTTGCCTTTGTTCAGTATC  (302 bp;
                               SEQ ID NO: 34)

β-actin:
GACATGGAGAAGATCTGGCAACCACA    (SEQ ID NO: 35)
and

ATCTCCTGCTCGAAGTCTAGAGCAA.    (440 bp;
                               SEQ ID NO: 36)
```

Statistical Analysis

One-way ANOVA (factorial) was used to compare groups. Sheffe' was used as a post hoc test. Values are expressed as mean+/−SD. A p value of less than 0.01 was considered significant.

Example 2

Suppressive ODN Inhibit Cytokine and Chemokine Production by RAW 264.7 Cells

Bacterial DNA contains immunostimulatory "CpG motifs" that trigger macrophages, monocytes and lymphocytes to produce a variety of pro-inflammatory cytokines and chemokines. The innate immune response elicited by CpG DNA reduces host susceptibility to infectious pathogens, and can also trigger detrimental inflammatory reactions. CpG motifs in bacterial DNA have been shown to cause inflammation of the lower respiratory tract (Schwartz et al., *J. Clin. Invest.* 100:68-73, 1997). In addition, sputum from subjects with cystic fibrosis contains bacterial DNA that causes acute inflammation when instilled intratracheally (Schwartz et al., *J. Clin. Invest.* 100:68-73, 1997). Thus, CpG ODN can be used as a surrogate for bacterial DNA in studying lung inflammation, and CpG-induced lung inflammation is a useful model for studying other, more typical causes of inflammatory lung disease.

Figure 2:
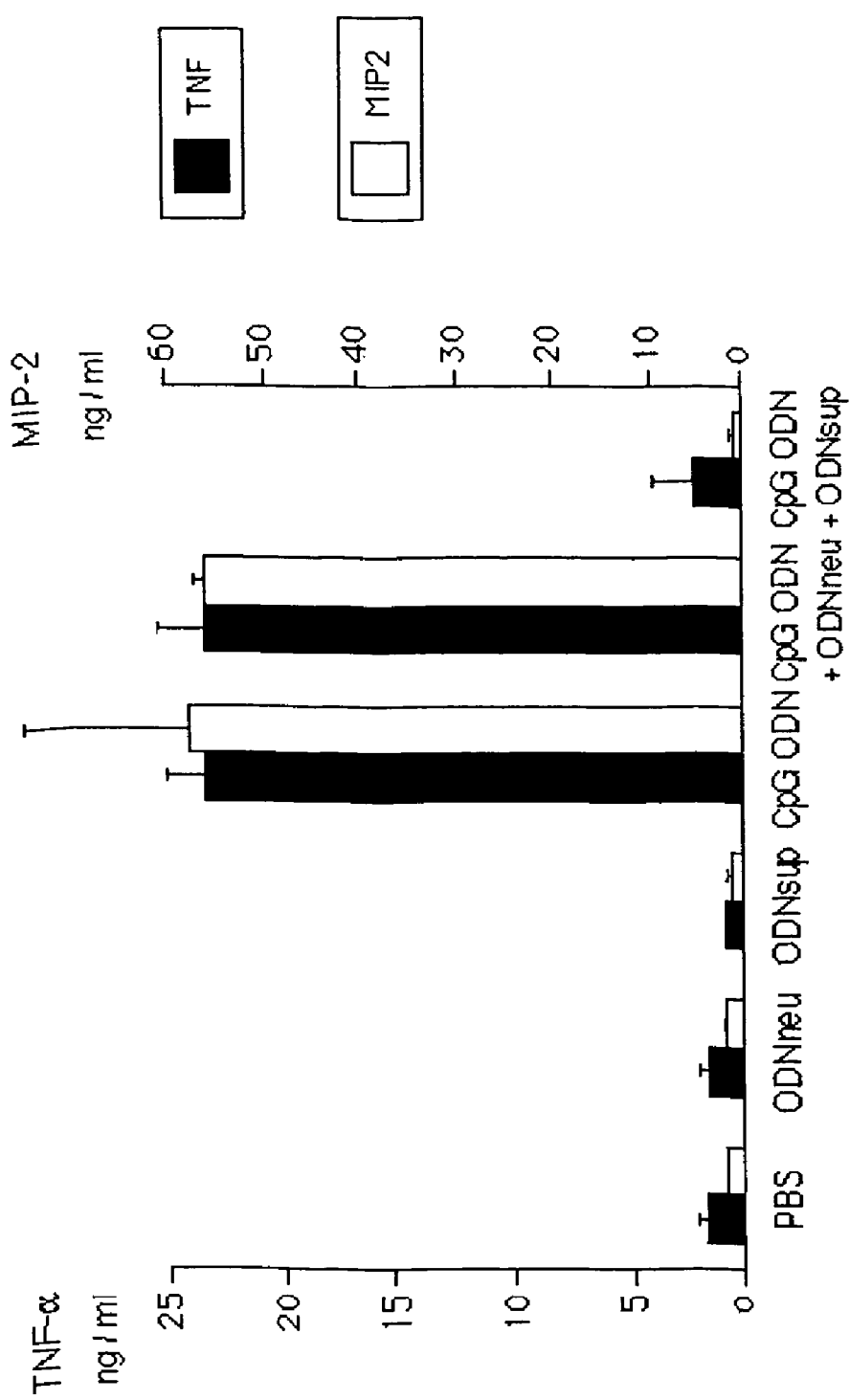
FIG. 2: is a graph showing that suppressive ODN significantly inhibits the production of TNFα (solid bar) and MIP-2 (open bar) induced by CpG ODN (p<0.01). RAW 264.7 cells were incubated with 1 μM of CpG ODN with or without 1 μM of another reagent. After 24 hours, the concentration of TNFα and MIP-2 in the supernatant was measured by ELISA. The experiments were repeated with similar results. Data are mean+/−SD. CpG ODN=synthetic oligodeoxynucleotide containing CpG motif; ODNneu=neutral ODN; suppressive ODN=suppressive ODN.

CpG DNA stimulates RAW 264.7 cells to produce a variety of cytokines and chemokines, including TNFα, IL-6, MIP-2 and KC. As seen in FIG. 2, adding an equimolar concentration of suppressive ODN to CpG-stimulated RAW 264.7 cells significantly reduces the production of these pro-inflammatory molecules. This effect was specific, as control ODN (lacking either stimulatory or suppressive motifs) had no effect or CpG-induced activation (FIG. 2).

Figure 3:
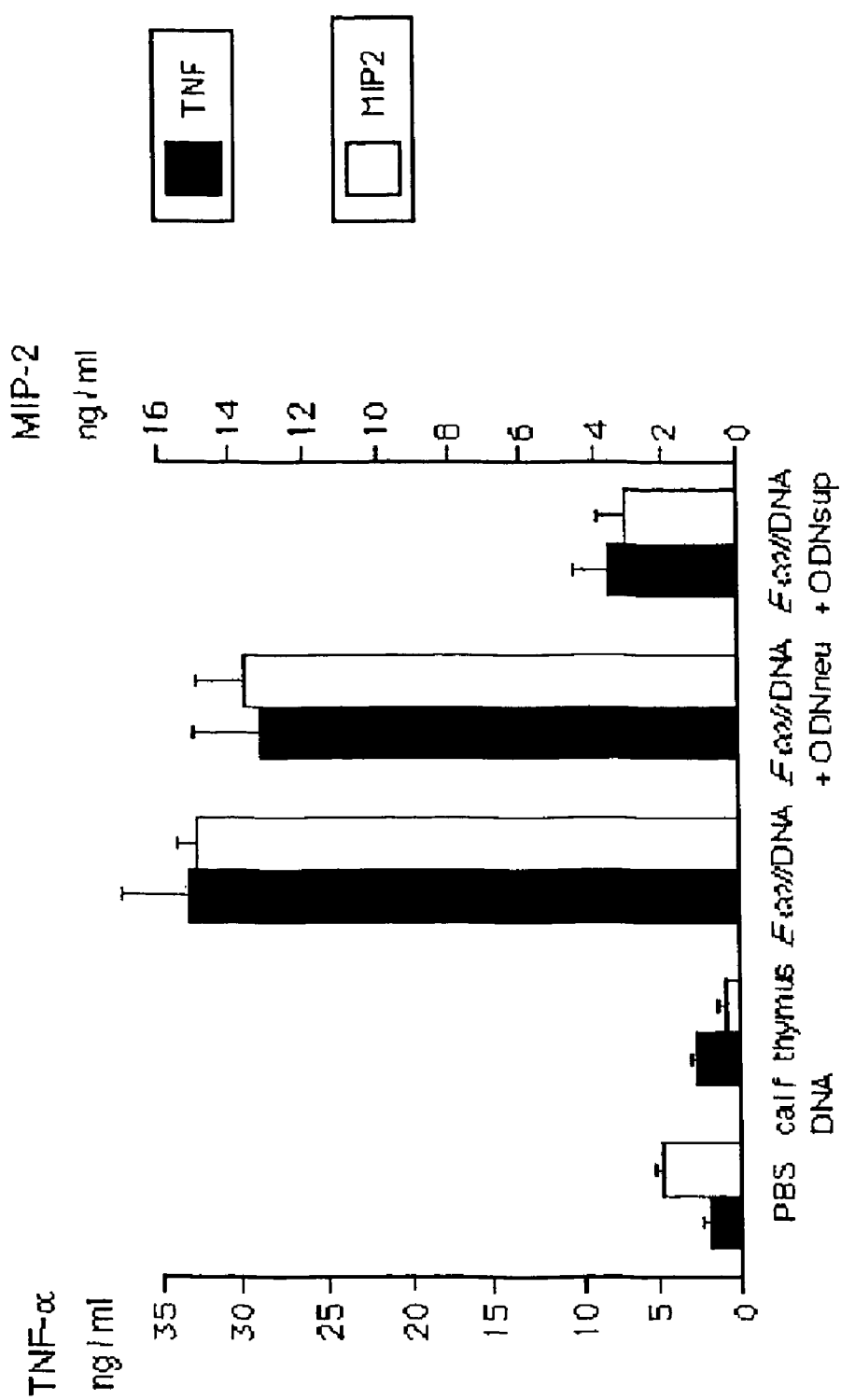
FIG. 3: is a graph showing that suppressive ODN significantly inhibits the production of TNFα (solid bar) and MIP-2 (open bar) induced by bacterial DNA that contains variety of CpG motifs (p<0.01). RAW 264.7 cells were incubated with 30 μg/ml of *E. coli* DNA with or without 5 μg/ml of another reagent. After 24 hours, the concentration of TNFα and MIP-2 in the supernatant was measured by ELISA. The experiments were repeated with similar results. Data are mean+/−SD.
Figure 4:
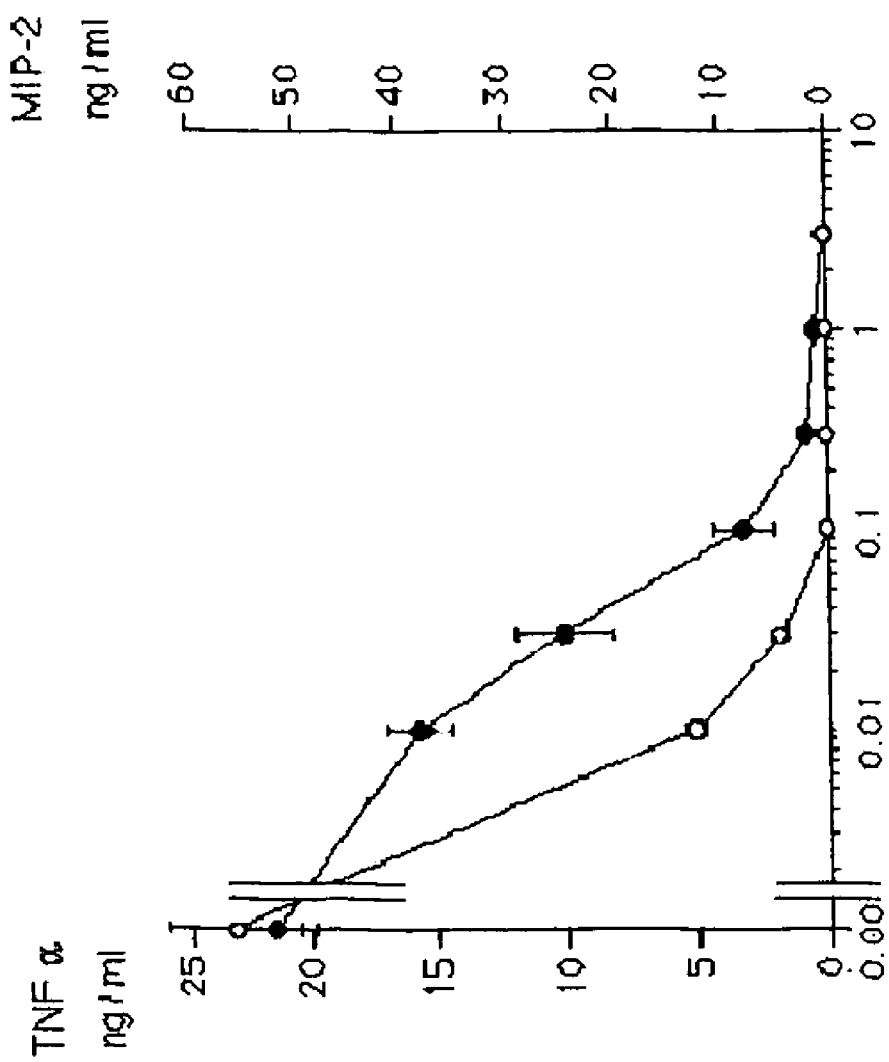
FIG. 4: is a graph showing that suppressive ODN inhibits the production of TNFα (closed circle) and MIP-2 (open circle) in a dose dependent manner. RAW 264.7 cells were incubated with 1 μM of CpG ODN with several concentrations of suppressive ODN. After 24 hours, the concentration of TNFα and MIP-2 in the supernatant was measured by ELISA. The experiments were repeated with similar results. Data are mean+/−SD.
Figure 5:
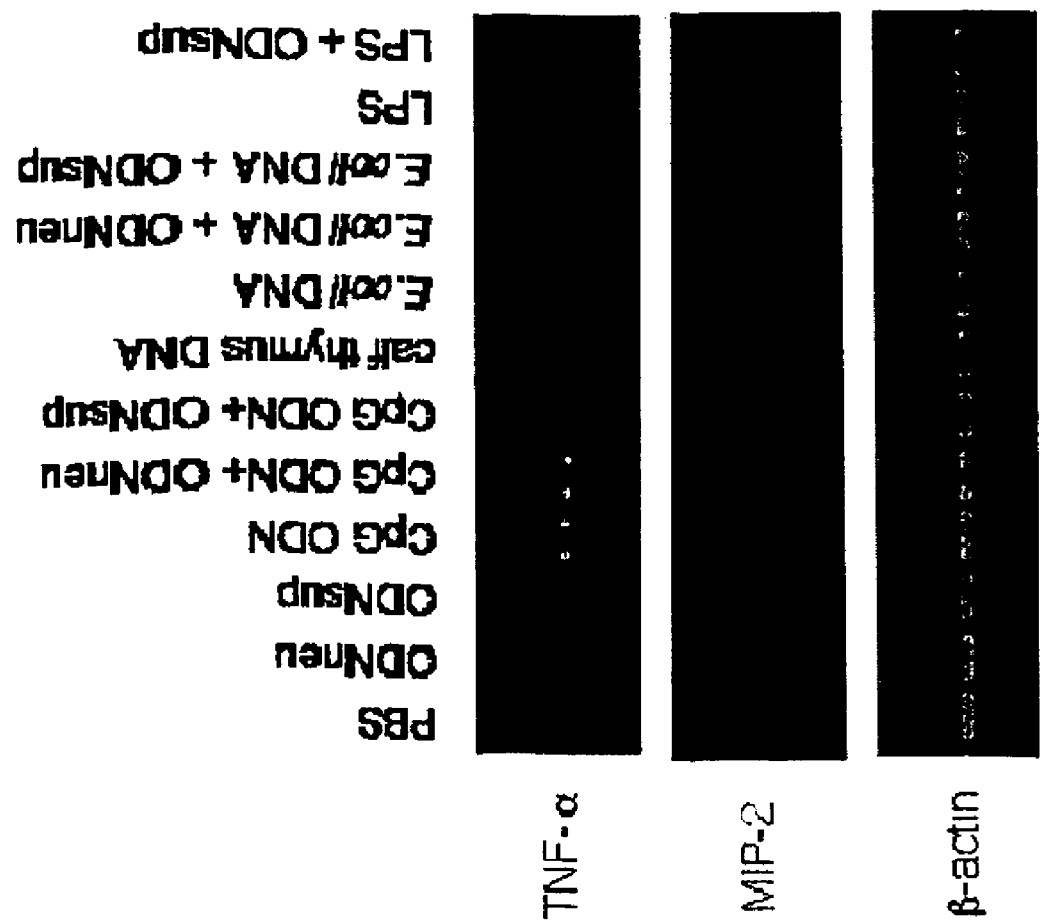
FIG. 5: is a digital image of a gel showing that suppressive ODN inhibits the expression of TNFα mRNA and MIP-2 mRNA by CpG ODN (lane 6) and by bacterial DNA (lane 10), but not by LPS (lane 12). RAW 264.7 cells were incubated with reagents indicated in the figure for 4 hours. Total mRNA was extracted, collected, and analyzed by reverse-transcription PCR (RT-PCR) assay.

Previous studies established that suppressive ODN inhibit CpG-induced immune activation in a dose-dependent manner. To confirm these findings, the effect of suppressive ODN on CpG-induced mRNA induction was evaluated by RT-PCR. After 4 hours of stimulation, cytokine and chemokine mRNA levels were significantly increased by CpG ODN (FIG. 3). This effect was significantly blocked by suppressive (but not control) ODN (FIG. 3).

Example 3

Suppressive ODN Blocks CpG-Induced Inflammation of the Mouse Lung

Figure 6:
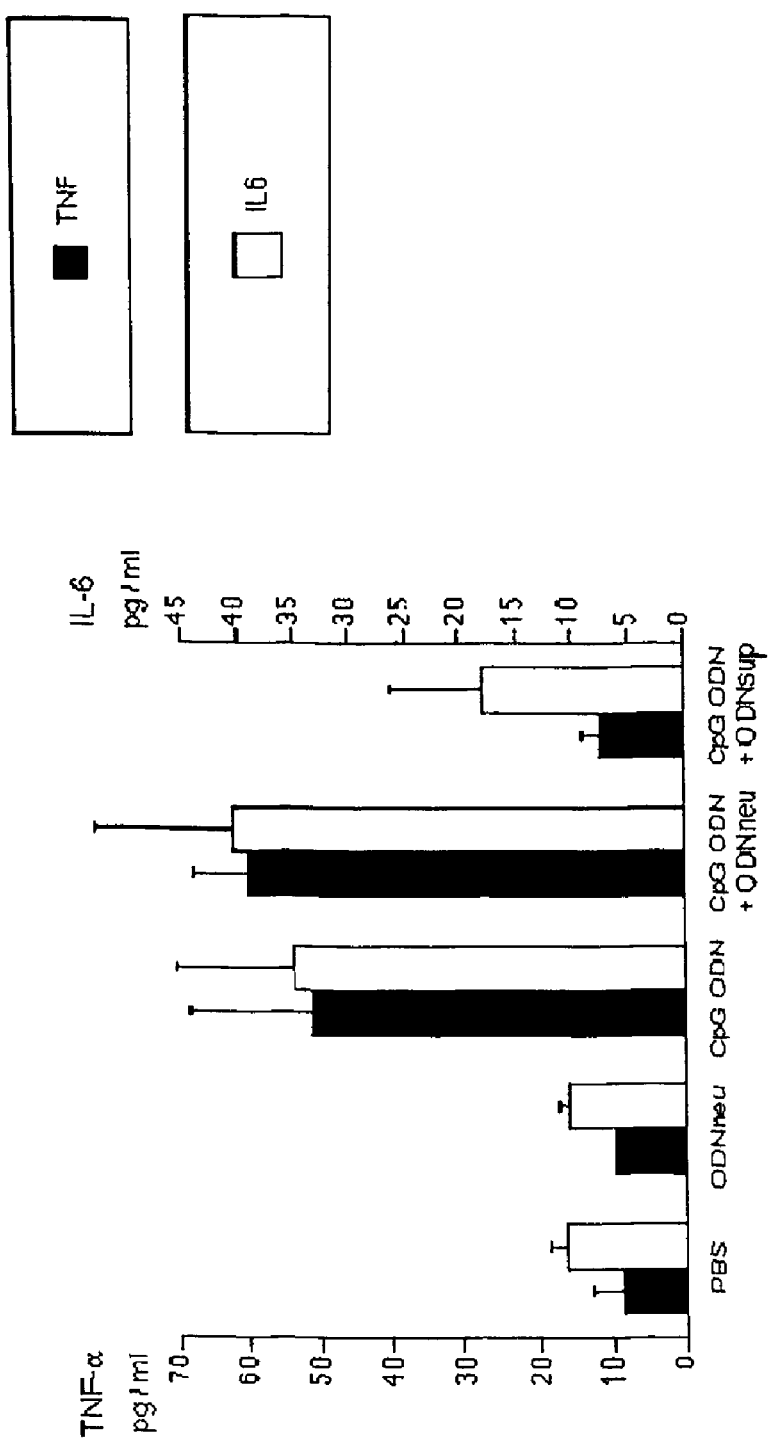
FIG. 6: is a graph showing that suppressive ODN significantly lowered the concentration of pro-inflammatory cytokines TNFα (solid bar) and IL-6 (open bar) in the BAL fluid (p<0.01). Thirty μg of CpG ODN was instilled into the lungs with or without 30 μg of another reagent. After 16 hours, mice were sacrificed and bronchoalveolar lavage was performed. The concentration of TNFα and IL-6 was measured by ELISA. Data are mean+/−SD.
Figure 7:
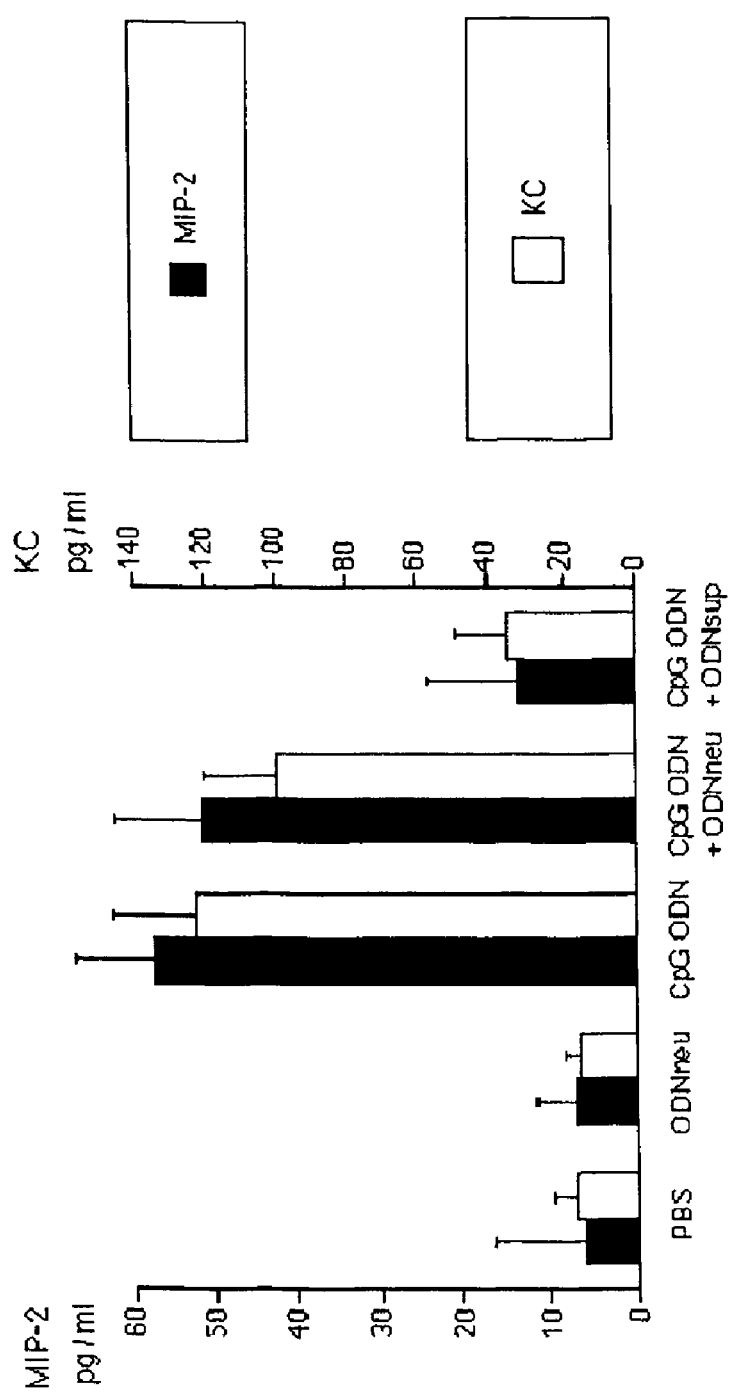
FIG. 7: is a graph showing that suppressive ODN significantly lowered the concentration of chemokines MIP-2 (solid bar) and KC (open bar) in the BAL fluid (p<0.01). Thirty μg of CpG ODN was intratracheally instilled with or without the same amount of another reagent. After 16 hours, mice were sacrificed and bronchoalveolar lavage was performed. The concentration of MIP-2 and KC was measured by ELISA. Data are mean+/−SD.
Figure 8:
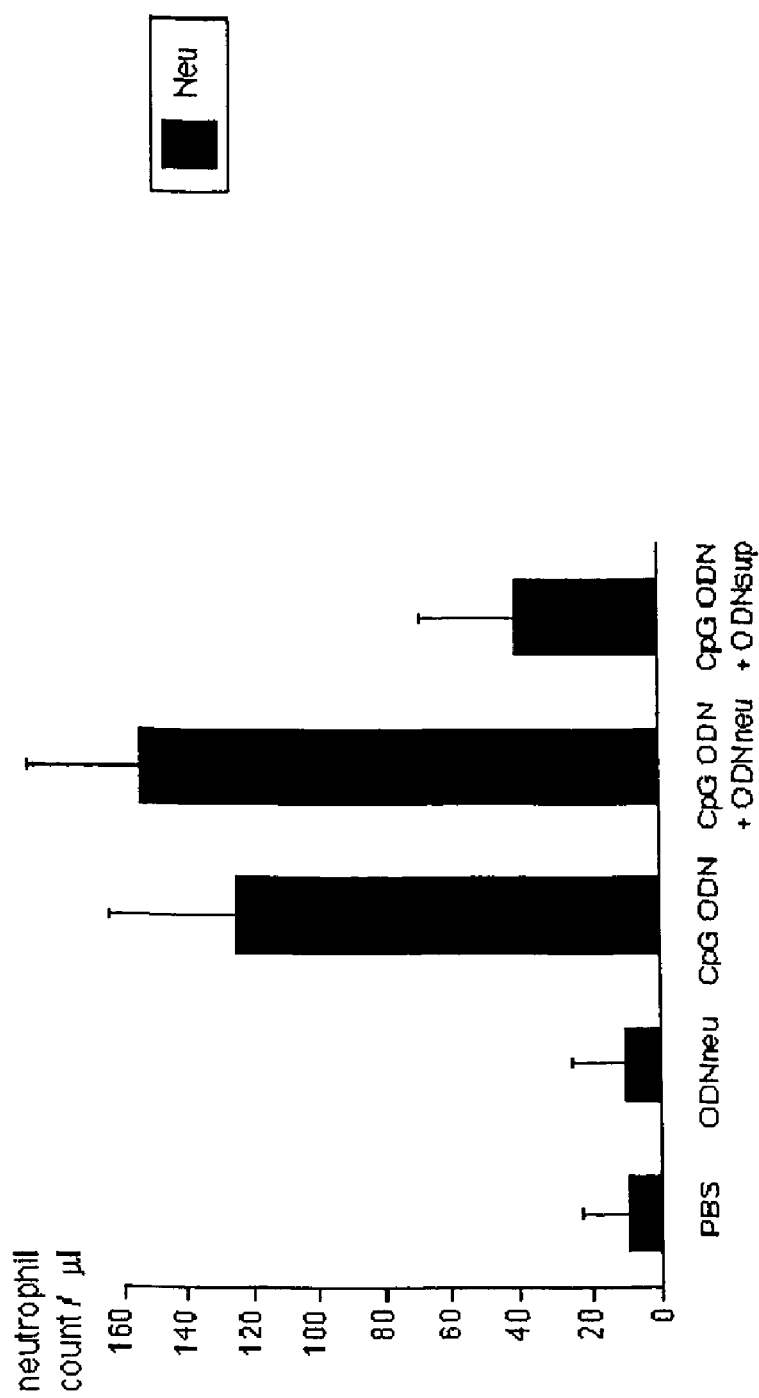
FIG. 8: is a graph showing that suppressive ODN significantly lowered the count of neutrophils in the BAL fluid (p<0.01). Thirty μg of CpG ODN was intratracheally instilled with or without 30 μg of another reagent. After 16 hours, mice were sacrificed and bronchoalveolar lavage was performed. The concentration of TNFα and IL-6 was measured by ELISA. Data are mean+/−SD.

Consistent with the findings of Schwartz et al. (*J. Clin. Invest.* 100:68-73, 1997), CpG DNA instilled into the lungs of normal mice triggers the production of pro-inflammatory cytokines and chemokines and significantly increases the number of neutrophils present in the BAL of normal mice (FIGS. 6-8). Preliminary studies established that these effects were maximal approximately 16 h after treatment. When suppressive ODNs were co-administered with the CpG DNA, the production of TNFα, IL-6, MIP-2m and KC were significantly reduced (p<0.001). Similarly, the number of infiltrating neutrophils was reduced (FIG. 8). Consistent with earlier findings, these effects were motif-specific, as control ODNs had no effect on CpG-induced lung inflammation.

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the following claims:

We claim:

1. A method of reducing the production of a cytokine or chemokine in a subject with an inflammatory lung disease, comprising administering to the subject with the inflammatory lung disease a suppressive oligodeoxynucleotide, wherein the oligodeoxynucleotide comprises from 2 to 4 guanosine-rich sequences and forms a G-tetrad, wherein the oligodeoxynucleotide comprises the nucleic acid sequence set forth as one of SEQ ID NO: 1, SEQ ID NO: 14, SEQ ID NO: 17, SEQ ID NO: 18, SEQ ID NO: 19, or SEQ ID NO: 21, wherein the oligodeoxynucleotide is 10 to 30 nucleotides in length, or a combination of two or more thereof, thereby reducing the production of the cytokine or chemokine in the subject with the inflammatory lung disease, wherein the cytokine or chemokine is tumor necrosis factor (TNF), macrophage inflammatory protein (MIP)-2, interleukin (IL)-6 or keratinocyte-derived chemokine (KC).

2. The method of claim 1, wherein the oligodeoxynucleotide is administered parenterally, orally, intravenously, intramuscularly, subcutaneously, intranasally, intratracheally or by inhalation.

3. The method of claim 1, wherein the inflammatory lung disease is acute respiratory distress syndrome, pneumonia, respiratory distress of prematurity, chronic bronchitis, chronic obstructive pulmonary disease, cystic fibrosis, pulmonary fibrosis, or pulmonary sarcoidosis.

4. The method of claim 3, wherein the inflammatory lung disease is acute respiratory distress syndrome.

5. The method of claim 1, wherein the oligodeoxynucleotide is administered by inhalation.

6. The method of claim 1, wherein the oligodeoxy nucleotide comprises the nucleic acid sequence set forth as SEQ ID NO: 14.

7. The method of claim 1, wherein the olidgodeoxynucleotide comprises the nucleic acid sequence set forth as SEQ ID NO: 17.

8. The method of claim 1, wherein the olidgodeoxynucleotide comprises the nucleic acid sequence set forth as SEQ ID NO: 18.

9. The method of claim 1, wherein the olidgodeoxynucleotide comprises the nucleic acid sequence set forth as SEQ ID NO: 19.

10. The method of claim 1, wherein the oligodeoxy nucleotide consists of the nucleic acid sequence set forth as SEQ ID NO: 21.

11. The method of claim 1, wherein the olidgodeoxynucleotide consists of the nucleic acid sequence set forth as SEQ ID NO: 14.

12. The method of claim 1, wherein the olidgodeoxynucleotide consists of the nucleic acid sequence set forth as SEQ ID NO: 18.

13. The method of claim 1, wherein the olidgodeoxynucleotide consists of the nucleic acid sequence set forth as SEQ ID NO: 19.

14. The method of claim 1, further comprising administering to the subject a therapeutically effective amount of an additional anti-inflammatory agent.

15. The method of claim 1, wherein the subject is a human.

16. The method of claim 1, further comprising administering to the subject an additional agent, wherein the agent is an anti-infective agent, bronchodilator, enzyme, expectorant, leukotriene antagonist, leukotriene formation inhibitor, or mast cell stabilizer.

17. The method of claim 1, wherein the oligodoexynucleotide is modified to prevent degradation.

18. The method of claim 1, wherein the oligodoexynucleotide comprises phosphorothioate nucleotides.

19. A method of reducing the production of a cytokine or chemokine in a subject, comprising administering to the subject a therapeutically effective amount of an oligodeoxynucleotide comprising the nucleic acid sequence set forth as SEQ ID NO: 1, wherein the oligodeoxynucleotide is 10 to 30 nucleotides in length, thereby reducing the production of the cytokine, wherein the cytokine is tumor necrosis factor (TNF) α, macrophage inflammatory protein (MIP)-2, interleukin (IL)-6 or keratinocyte-derived cytokine (KC), wherein the subject has an inflammatory lung disease.

20. The method of claim 19, wherein the oligodeoxynucleotide is administered by inhalation.

21. The method of claim 19, wherein the olidgodeoxynucleotide consists of the nucleic acid sequence set forth as SEQ ID NO: 1.

22. The method of claim 19, wherein the subject is human.

23. The method of claim 19, wherein the inflammatory lung disease is acute respiratory distress syndrome, pneumonia, respiratory distress of prematurity, chronic bronchitis, chronic obstructive pulmonary disease, cystic fibrosis, pulmonary fibrosis, or pulmonary sarcoidosis.

24. The method of claim 19, wherein the subject has acute respiratory distress syndrome.

25. The method of claim 19, further comprising administering to the subject a therapeutically effective amount of an additional anti-inflammatory agent.

26. The method of claim 19, wherein the oligodeoxynucleotide is administered parenterally, orally, intravenously, intramuscularly, subcutaneously, intranasally, intratracheally or by inhalation.

27. The method of claim 19, further comprising administering to the subject an additional agent, wherein the agent is an anti-infective agent, bronchodilator, enzyme, expectorant, leukotriene antagonist, leukotriene formation inhibitor, or mast cell stabilizer.

28. A method of reducing the production of a cytokine or chemokine in a cell in vitro, comprising contacting the cell with a suppressive oligodeoxynucleotide, wherein the suppressive oligodeoxynucleotide comprises the nucleic acid sequence set forth as one of SEQ ID NO: 1, SEQ ID NO: 14, SEQ ID NO: 17, SEQ ID NO: 18, SEQ ID NO: 19, SEQ ID NO: 21, or a combination of two or more thereof, wherein the oligodeoxynucleotide is 10 to 30 nucleotides in length, and wherein the cytokine is tumor necrosis factor (TNF)α, macrophage inflammatory protein (MIP)-2, interleukin (IL) 6 or keratinocyte-derived cytokine (KC).

29. The method of claim 28, wherein the suppressive oligodeoxynucleotide consists of the nucleic acid sequence set forth as one of SEQ ID NO: 1, SEQ ID NO: 14, SEQ ID NO: 17, SEQ ID NO: 18, SEQ ID NO: 19, or SEQ ID NO: 21.

* * * * *

SEQUENCE LISTING

<160> NUMBER OF SEQ ID NOS: 36

<210> SEQ ID NO 1
<211> LENGTH: 16
<212> TYPE: DNA

-continued

```
<213> ORGANISM: Artificial Sequence
<220> FEATURE:
<223> OTHER INFORMATION: Suppressive oligonucleotide sequence.

<400> SEQUENCE: 1
cctcaagctt gagggg                                                         16

<210> SEQ ID NO 2
<211> LENGTH: 24
<212> TYPE: DNA
<213> ORGANISM: Artificial Sequence
<220> FEATURE:
<223> OTHER INFORMATION: Suppressive oligonucleotide sequence.

<400> SEQUENCE: 2
ttagggttag ggttagggtt aggg                                                24

<210> SEQ ID NO 3
<211> LENGTH: 18
<212> TYPE: DNA
<213> ORGANISM: Artificial Sequence
<220> FEATURE:
<223> OTHER INFORMATION: Suppressive oligonucleotide sequence.

<400> SEQUENCE: 3
ttagggttag ggttaggg                                                       18

<210> SEQ ID NO 4
<211> LENGTH: 12
<212> TYPE: DNA
<213> ORGANISM: Artificial Sequence
<220> FEATURE:
<223> OTHER INFORMATION: Suppressive oligonucleotide sequence.

<400> SEQUENCE: 4
ttagggttag gg                                                             12

<210> SEQ ID NO 5
<211> LENGTH: 24
<212> TYPE: DNA
<213> ORGANISM: Artificial Sequence
<220> FEATURE:
<223> OTHER INFORMATION: Suppressive oligonucleotide sequence.

<400> SEQUENCE: 5
tgggcggttg ggcggttggg cggt                                                24

<210> SEQ ID NO 6
<211> LENGTH: 16
<212> TYPE: DNA
<213> ORGANISM: Artificial Sequence
<220> FEATURE:
<223> OTHER INFORMATION: Suppressive oligonucleotide sequence.

<400> SEQUENCE: 6
tgggcggttg ggcggt                                                         16

<210> SEQ ID NO 7
<211> LENGTH: 16
<212> TYPE: DNA
<213> ORGANISM: Artificial Sequence
<220> FEATURE:
<223> OTHER INFORMATION: Suppressive oligonucleotide sequence.

<400> SEQUENCE: 7
tcaaccttca ttaggg                                                         16
```

```
<210> SEQ ID NO 8
<211> LENGTH: 22
<212> TYPE: DNA
<213> ORGANISM: Artificial Sequence
<220> FEATURE:
<223> OTHER INFORMATION: Suppressive oligonucleotide sequence.

<400> SEQUENCE: 8
ttagggttag ggtcaacctt ca                                              22

<210> SEQ ID NO 9
<211> LENGTH: 22
<212> TYPE: DNA
<213> ORGANISM: Artificial Sequence
<220> FEATURE:
<223> OTHER INFORMATION: Suppressive oligonucleotide sequence.

<400> SEQUENCE: 9
tcaaccttca ttagggttag gg                                              22

<210> SEQ ID NO 10
<211> LENGTH: 22
<212> TYPE: DNA
<213> ORGANISM: Artificial Sequence
<220> FEATURE:
<223> OTHER INFORMATION: Suppressive oligonucleotide sequence.

<400> SEQUENCE: 10
gggttagggt tatcaacctt ca                                              22

<210> SEQ ID NO 11
<211> LENGTH: 22
<212> TYPE: DNA
<213> ORGANISM: Artificial Sequence
<220> FEATURE:
<223> OTHER INFORMATION: Suppressive oligonucleotide sequence.

<400> SEQUENCE: 11
tcaaccttca gggttagggt ta                                              22

<210> SEQ ID NO 12
<211> LENGTH: 22
<212> TYPE: DNA
<213> ORGANISM: Artificial Sequence
<220> FEATURE:
<223> OTHER INFORMATION: Suppressive oligonucleotide sequence.

<400> SEQUENCE: 12
gggtgggtgg gtattaccat ta                                              22

<210> SEQ ID NO 13
<211> LENGTH: 22
<212> TYPE: DNA
<213> ORGANISM: Artificial Sequence
<220> FEATURE:
<223> OTHER INFORMATION: Suppressive oligonucleotide sequence.

<400> SEQUENCE: 13
attaccatta gggtgggtgg gt                                              22

<210> SEQ ID NO 14
<211> LENGTH: 18
<212> TYPE: DNA
<213> ORGANISM: Artificial Sequence
<220> FEATURE:
<223> OTHER INFORMATION: Suppressive oligonucleotide sequence.
```

```
<400> SEQUENCE: 14
tgggcggttc aagcttga                                                18

<210> SEQ ID NO 15
<211> LENGTH: 18
<212> TYPE: DNA
<213> ORGANISM: Artificial Sequence
<220> FEATURE:
<223> OTHER INFORMATION: Suppressive oligonucleotide sequence.

<400> SEQUENCE: 15
tcaagcttca tgggcggt                                                18

<210> SEQ ID NO 16
<211> LENGTH: 22
<212> TYPE: DNA
<213> ORGANISM: Artificial Sequence
<220> FEATURE:
<223> OTHER INFORMATION: Suppressive oligonucleotide sequence.

<400> SEQUENCE: 16
gggtgggtgg gtagacgtta cc                                           22

<210> SEQ ID NO 17
<211> LENGTH: 16
<212> TYPE: DNA
<213> ORGANISM: Artificial Sequence
<220> FEATURE:
<223> OTHER INFORMATION: Suppressive oligonucleotide sequence.

<400> SEQUENCE: 17
ggggggtcaa gcttca                                                  16

<210> SEQ ID NO 18
<211> LENGTH: 16
<212> TYPE: DNA
<213> ORGANISM: Artificial Sequence
<220> FEATURE:
<223> OTHER INFORMATION: Suppressive oligonucleotide sequence.

<400> SEQUENCE: 18
tcaagcttca gggggg                                                  16

<210> SEQ ID NO 19
<211> LENGTH: 16
<212> TYPE: DNA
<213> ORGANISM: Artificial Sequence
<220> FEATURE:
<223> OTHER INFORMATION: Suppressive oligonucleotide sequence.

<400> SEQUENCE: 19
ggggggtcaa cgttca                                                  16

<210> SEQ ID NO 20
<211> LENGTH: 20
<212> TYPE: DNA
<213> ORGANISM: Artificial Sequence
<220> FEATURE:
<223> OTHER INFORMATION: Suppressive oligonucleotide sequence.

<400> SEQUENCE: 20
gagcaagctg gaccttccat                                              20

<210> SEQ ID NO 21
<211> LENGTH: 21
<212> TYPE: DNA
```

```
<213> ORGANISM: Artificial Sequence
<220> FEATURE:
<223> OTHER INFORMATION: Suppressive oligonucleotide sequence.

<400> SEQUENCE: 21
gagcaagctg gtagacgtta g                                            21

<210> SEQ ID NO 22
<211> LENGTH: 20
<212> TYPE: DNA
<213> ORGANISM: Artificial Sequence
<220> FEATURE:
<223> OTHER INFORMATION: Suppressive oligonucleotide sequence.

<400> SEQUENCE: 22
gggcaagctg gacctggggg                                              20

<210> SEQ ID NO 23
<211> LENGTH: 20
<212> TYPE: DNA
<213> ORGANISM: Artificial Sequence
<220> FEATURE:
<223> OTHER INFORMATION: Suppressive oligonucleotide sequence.

<400> SEQUENCE: 23
ggggaagctg gacctggggg                                              20

<210> SEQ ID NO 24
<211> LENGTH: 20
<212> TYPE: DNA
<213> ORGANISM: Artificial Sequence
<220> FEATURE:
<223> OTHER INFORMATION: Suppressive oligonucleotide sequence.

<400> SEQUENCE: 24
gggcaagctg gaccttcggg                                              20

<210> SEQ ID NO 25
<211> LENGTH: 22
<212> TYPE: DNA
<213> ORGANISM: Artificial Sequence
<220> FEATURE:
<223> OTHER INFORMATION: Suppressive oligonucleotide sequence.

<400> SEQUENCE: 25
ggcaagctgg accttcgggg gg                                           22

<210> SEQ ID NO 26
<211> LENGTH: 15
<212> TYPE: DNA
<213> ORGANISM: Artificial Sequence
<220> FEATURE:
<223> OTHER INFORMATION: Neutral oligonucleotide sequence.

<400> SEQUENCE: 26
gctagatgtt agcgt                                                   15

<210> SEQ ID NO 27
<211> LENGTH: 15
<212> TYPE: DNA
<213> ORGANISM: Artificial Sequence
<220> FEATURE:
<223> OTHER INFORMATION: Stimulatory oligonucleotide sequence.

<400> SEQUENCE: 27
gctagacgtt agcgt                                                   15
```

<210> SEQ ID NO 28
<211> LENGTH: 20
<212> TYPE: DNA
<213> ORGANISM: Artificial Sequence
<220> FEATURE:
<223> OTHER INFORMATION: Neutral oligonucleotide sequence.
<220> FEATURE:
<221> NAME/KEY: modified_base
<222> LOCATION: (10)..(11)
<223> OTHER INFORMATION: Modified guanosine base.

<400> SEQUENCE: 28
gagcaagctg gaccttccat          20

<210> SEQ ID NO 29
<211> LENGTH: 21
<212> TYPE: DNA
<213> ORGANISM: Artificial Sequence
<220> FEATURE:
<223> OTHER INFORMATION: Neutral oligonucleotide sequence.
<220> FEATURE:
<221> NAME/KEY: modified_base
<222> LOCATION: (3)..(3)
<223> OTHER INFORMATION: Modified guanosine base.
<220> FEATURE:
<221> NAME/KEY: modified_base
<222> LOCATION: (10)..(10)
<223> OTHER INFORMATION: Modified guanosine base.

<400> SEQUENCE: 29
gagcaagctg gtagacgtta g          21

<210> SEQ ID NO 30
<211> LENGTH: 21
<212> TYPE: DNA
<213> ORGANISM: Artificial Sequence
<220> FEATURE:
<223> OTHER INFORMATION: Neutral oligonucleotide sequence.
<220> FEATURE:
<221> NAME/KEY: modified_base
<222> LOCATION: (1)..(1)
<223> OTHER INFORMATION: Modified guanosine base.
<220> FEATURE:
<221> NAME/KEY: modified_base
<222> LOCATION: (10)..(10)
<223> OTHER INFORMATION: Modified guanosine base.

<400> SEQUENCE: 30
gagcaagctg gtagacgtta g          21

<210> SEQ ID NO 31
<211> LENGTH: 21
<212> TYPE: DNA
<213> ORGANISM: Artificial Sequence
<220> FEATURE:
<223> OTHER INFORMATION: Oigonucleotide primer.

<400> SEQUENCE: 31
atgagcacag aaagcatgat c          21

<210> SEQ ID NO 32
<211> LENGTH: 21
<212> TYPE: DNA
<213> ORGANISM: Artificial Sequence
<220> FEATURE:
<223> OTHER INFORMATION: Oigonucleotide primer.

<400> SEQUENCE: 32
tacaggcttg tcactcgaat t          21

```
<210> SEQ ID NO 33
<211> LENGTH: 25
<212> TYPE: DNA
<213> ORGANISM: Artificial Sequence
<220> FEATURE:
<223> OTHER INFORMATION: Oigonucleotide primer.

<400> SEQUENCE: 33 atggccctc ccacctgccg gctcc                                          25

<210> SEQ ID NO 34
<211> LENGTH: 28
<212> TYPE: DNA
<213> ORGANISM: Artificial Sequence
<220> FEATURE:
<223> OTHER INFORMATION: Oigonucleotide primer.

<400> SEQUENCE: 34
tcagttagcc ttgcctttgt tcagtatc                                      28

<210> SEQ ID NO 35
<211> LENGTH: 26
<212> TYPE: DNA
<213> ORGANISM: Artificial Sequence
<220> FEATURE:
<223> OTHER INFORMATION: Oigonucleotide primer.

<400> SEQUENCE: 35
gacatggaga agatctggca accaca                                        26

<210> SEQ ID NO 36
<211> LENGTH: 25
<212> TYPE: DNA
<213> ORGANISM: Artificial Sequence
<220> FEATURE:
<223> OTHER INFORMATION: Oigonucleotide primer.

<400> SEQUENCE: 36
atctcctgct cgaagtctag agcaa                                         25
```